(12) United States Patent
Yang et al.

(10) Patent No.: US 8,961,439 B2
(45) Date of Patent: Feb. 24, 2015

(54) SYSTEM AND METHOD FOR ANALYZING GAIT USING FABRIC SENSORS

(75) Inventors: Chang-Ming Yang, Jhunan Township (TW); Tzu Lin Yang, Jhongshan District (TW); Ching Wen Yang, Datong District (TW); Hao Yang, Taipei (TW)

(73) Assignee: Ming Young Biomedical Corp., Miaoli (TW)

( * ) Notice: Subject to any disclaimer, the term of this patent is extended or adjusted under 35 U.S.C. 154(b) by 198 days.

(21) Appl. No.: 13/412,286

(22) Filed: Mar. 5, 2012

(65) Prior Publication Data

US 2012/0253234 A1 Oct. 4, 2012

Related U.S. Application Data

(63) Continuation-in-part of application No. PCT/CN2009/000999, filed on Sep. 3, 2009, and a continuation-in-part of application No. PCT/CN2010/001341, filed on Sep. 3, 2010.

(51) Int. Cl.
   *A61B 5/00* (2006.01)

(52) U.S. Cl.
   USPC .......................................................... 600/595

(58) Field of Classification Search
   USPC ................................................. 600/592, 595
   See application file for complete search history.

(56) References Cited

U.S. PATENT DOCUMENTS

| | | | | |
|---|---|---|---|---|
| 5,546,955 A | * | 8/1996 | Wilk | 600/549 |
| 6,922,592 B2 | * | 7/2005 | Thompson et al. | 607/59 |
| 7,770,473 B2 | * | 8/2010 | Von Lilienfeld-Toal et al. | 73/862.68 |
| 7,771,371 B2 | * | 8/2010 | Avni | 600/592 |
| 8,028,443 B2 | * | 10/2011 | Case, Jr. | 36/132 |
| 8,188,868 B2 | * | 5/2012 | Case, Jr. | 340/573.1 |
| 2008/0146968 A1 | | 6/2008 | Hanawaka et al. | |
| 2008/0287832 A1 | | 11/2008 | Collins et al. | |

FOREIGN PATENT DOCUMENTS

| | | |
|---|---|---|
| CN | 2040365 U | 7/1989 |
| CN | 200994779 Y | 12/2007 |
| CN | 201135440 Y | 10/2008 |
| WO | 01/39655 A2 | 6/2001 |
| WO | 2005/037103 A1 | 4/2005 |
| WO | 2008/058048 A2 | 5/2008 |

OTHER PUBLICATIONS

International Search Report w/translation from PCT/CN2010/001341 dated Dec. 9, 2010 (7 pages).
International Search Report w/translation from PCT/CN2009/000999 dated Jun. 10, 2010 (4 pages).

* cited by examiner

*Primary Examiner* — Max Hindenburg
(74) *Attorney, Agent, or Firm* — Osha Liang LLP

(57) ABSTRACT

A system for analyzing gait using textile sensors is disclosed. A system includes a sock sensing system, which comprises a sock and at least one switch, tension sensor, or pressure sensor for sensing a posture or movement; and a processor configured to receive signals from the sock sensing system and to analyze a gait parameter, wherein the processor is configured to calculate the gait parameter using a signal from the sock sensing system as a trigger point.

18 Claims, 24 Drawing Sheets

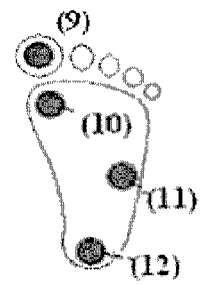
Fig. 3A        Fig. 3B
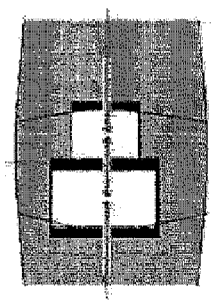
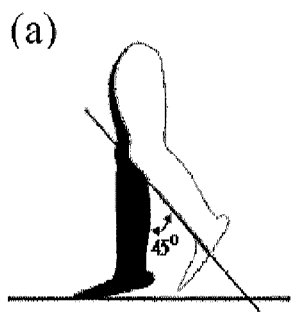
Fig. 4A        Fig. 4B
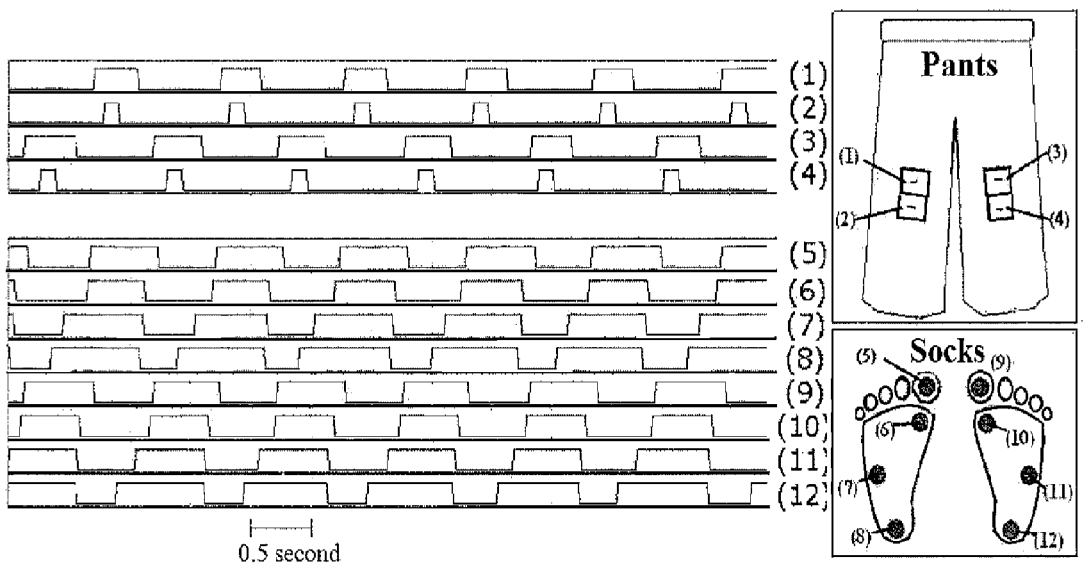
Fig. 5

SYSTEM AND METHOD FOR ANALYZING GAIT USING FABRIC SENSORS

TECHNICAL FIELD

Embodiments of the present invention can be applied to rehabilitation, physical training, long-term care, orthopedic and sports medicine, health, entertainment and other fields. Embodiments of the present invention relate to a system and a method for sensing and analyzing the wearer's foot movements and understanding the physiological state of the wearer by using textile sensor being fixed to the clothing.

Gait analysis is commonly used to help athletes and patients with impaired motor function, such as patients with cerebral palsy, Parkinson's disease, stroke or accidental injury. Gait analysis of existing technologies is often conducted in specialized laboratories or physicians' consulting rooms and can only be completed by using many sophisticated devices and complex methods. However, the optimal gait analysis system should be able to achieve continuous real time monitoring at low cost and easy to operate and obtain. Existing technology has another defect: it cannot reflect the motor function of the user in the daily life. Therefore, experts and patients need a low-cost system to achieve quantitative and reproducible results. Gait analysis is currently mostly used to help athletes and the injured which is mainly conducted in laboratories or physicians' consulting rooms through visual observation. Clinicians rely on a wide range of gait analysis, diagnosis and treatment, but are facing many complex factors. Gait analysis systems and procedures for general users have the benefits of continuous monitoring, low price and easy to use and obtain. However, the traditional gait analysis equipment usually requires field tests, or comprehensive gait analysis experiments in laboratories, which goes against the popularity of gait analysis system.

Due to the high threshold, gait analysis can provide substantial and repeatable read data in a timely manner and monitor the user's gait signal and help the injured users and patients suffering from Parkinson's disease. However, as currently it is rather difficult to obtain gait analysis device or due to limitations in application of related products themselves, there is no way to meet the consumer demands. For example, both U.S. Pat. Nos. 6,789,331 and 7,168,185 disclose methods of using shoes as gait sensors. However, the shoes cannot be washed, thus causing inconvenience to the users. U.S. Pat. No. 6,231,527 discloses a method of coupling a video camera with shoes to form gait analysis sensors, and the gait analysis can only be conducted in rooms. Thus, operation is inconvenient for users and not conducive to the promotion of gait analysis system.

U.S. Pat. No. 6,984,208 discloses a method of testing user's posture and movement states with ultrasound and analyzing related data of gait analysis. However, as ultrasound equipment is rather expensive, it is not conducive to the promotion of gait analysis system. U.S. patent No. 20080108913A1 discloses a method of detecting the user's fall with pressure sensor. However, each shoe or sock has to be equipped with an independent power supply, but not digital sensor. Meanwhile, in signal processing, feedback method has to be adopted for signal analysis. The process is too cumbersome, lengthy and complex and needs to use fuzzy logics for preventing falls. The system can neither show the user's gait parameters nor sense the body posture or movement. It can only produce a feedback value in accordance with the data and stability profile measured by the pressure sensor and mainly focuses on determining the ideal central mass profile and mass of individual so as to prevent falls. As described therein, accelerometer can be used for measuring the gait speed, stride length and gait time. In our present design, we improve the original design and replace the accelerometer with only switch, pressure, tension and other textile sensors for simultaneously forecasting the gait parameters and movements of knees, hips, hands and other parts and detecting stride length, speed, accelerated speed, angle of ankle joint, angular speed and other gait parameters. Feedback value is no longer needed. Sock sensors may directly calculate the gait parameters or body posture and movement.

U.S. patent No. US20090012433A1 discloses a method of detecting user's gait parameters with cameras, microphones and a sensor and analyzing relevant data. However, the analysis method is too cumbersome and not conducive to the promotion of gait analysis. U.S. patent No. US200610282021A1 discloses a method of detecting user's posture and gait with a sensor and a remote monitoring system and analyzing relevant data. However, the system has distance constraints. The monitor cannot process the relevant information when the user is too far away from it. U.S. patent No. US2007/0112287 A1 discloses a method of handing accelerometers and gyroscopes on the ears of users so as to detect the gait analysis data of users. However, too high cost is not conducive to the promotion.

People wear clothes and sit on chair or lie in bed in most of the time in daily life. Thus, physiological function may be sensed during body movement by setting gait sensor on pants, socks or clothing and connecting the gait sensor to a physiological sensing device such as sensor for sensing heartbeat, respiration, body temperature, sweat, blood oximeter, ECG and so on. Hence, embodiments of the present invention can be further extended to every aspect of daily life for measuring the gait of users in different postures and thereby analyzing the physiological state of users. With the sensor being previously set in shoes, the gait analysis might generate great error if the gait sensor was not in exact match with feet. Moreover, it was difficult to match different shoes and too expensive and current consuming. In embodiments of the present invention, sensor is set in socks and thus comfortable and washable. Relevant data for gait analysis may be measured even a user wears different shoes. It is suitable for different users because socks have no such accurate size requirements as shoes. Instead, socks can completely fit the feet of users and obtain more accurate gait analysis results. The sock sensor in embodiments of the present invention may sense different shoes a user wears when he is walking and learn the style of shoes with the aid of gait analysis signal, such as high heels, low cutters, slippers, sneakers and skating shoes etc. Embodiments of the present invention sock sensor can be configured in different shoes and is easy to use for users and ergonomic. The sock sensors can be applied in a variety of shoes. Thus, long time and continuous physiological function and gait analysis variation diagrams could be integrated and this is of great help to health and safety of users. As gait sensors are installed in one or more daily life clothes in contact with body, it is conducive to promotion and application of embodiments of the present invention. At present, this technology has passed the review of IEEE, EMBC 2009 annual session and the paper entitled "*A wireless gait analysis system by digital textile sensors*" is to be published in September. This technology has passed the review of IEEE, EMBC 2010 annual session and the paper titled "*Sensing of Wearable Digital Textile Sensor with Body Motion Analysis*" is to be published. Finally, the invention is applicable not only to humans. For behavior patterns of animals such as cat, dog and so on, the invention may be applied for long term monitoring analysis and prediction of behavior patterns.

An objective of the present invention is to sense gait analysis and posture changes, such as angle of bending of knee joint, stride length, the number of steps per minute and walking speed and if the heel is upon the earth or not, arms are swinging or not and the waist is bent or not with sensors in clothes and pants besides sensors in socks. Sequence and cycle of changes of various postures and other parameters are used to observe the health condition or rehabilitation treatment effects of users, or determine the posture of users (such as walking forward, walking backward, running, climbing stairs, walking down the stairs, climbing up, climbing down hill, walking sideways, falling). The invention may be used as an input of interactive computer games, other than just virtual computer games in which the player shows no actual interactive action with the game software. It may also be applied to detect the user's posture while driving (for example: the degree of foot bending of the driver when he applying the brake). Embodiments of the present invention relate to a wearable gait analysis system with the following structure characteristics: first, the gait analysis device is wearable and comfortable and can be installed directly on general pants or socks and thus rather convenient in daily life; second, using wireless transmission technology, the user will not be disturbed in test; third, the wearable gait analysis system has the following features: washable, durable, elastic, flexible and squeezable, thus being convenient for use in daily life; fourth, with digital output and Bluetooth interfaces, the measured data can be sent directly to common instruments in daily life for signal analysis, such as PDA or notebook computer. Thus, such electronic devices that can be easily obtained may be used for testing a user's posture and relevant data for gait analysis and the variability and stability of each parameter can also be presented with Power Spectrum; and fifth, the user's body weight and changes could be detected. Another objective of the present invention is, another reference area is set in the surrounding area where the transmission line is not insulated for detecting leakage of fabrics, for example, the fabric is wet or the transmission line and the reference area suffer from short circuit.

BRIEF DESCRIPTION OF THE DRAWINGS

FIG. 3A illustrates a location plan of a sensor in a sock in accordance with one embodiment of the present invention. FIG. 3B illustrates a relative location plan of a sensor in a sock in accordance with one embodiment of the present invention.

FIG. 4A illustrates a location plan of a sensor on a knee in accordance with one embodiment of the present invention. FIG. 4B illustrates a location plan of a tension sensor being installed in pants in accordance with one embodiment of the present invention.

FIG. 5 illustrates a typical timing sequence diagram and sensor location plan in accordance with one embodiment of the present invention.

DETAILED DESCRIPTION

In order to further clarify the technical means adopted to achieve the objectives of the present invention as well as effects, the following details the gait analysis system using textile sensors, as well as modes of application, structures, characteristics and effects of the method, device and system by accompanying drawings and preferred embodiments.

Figure 1:
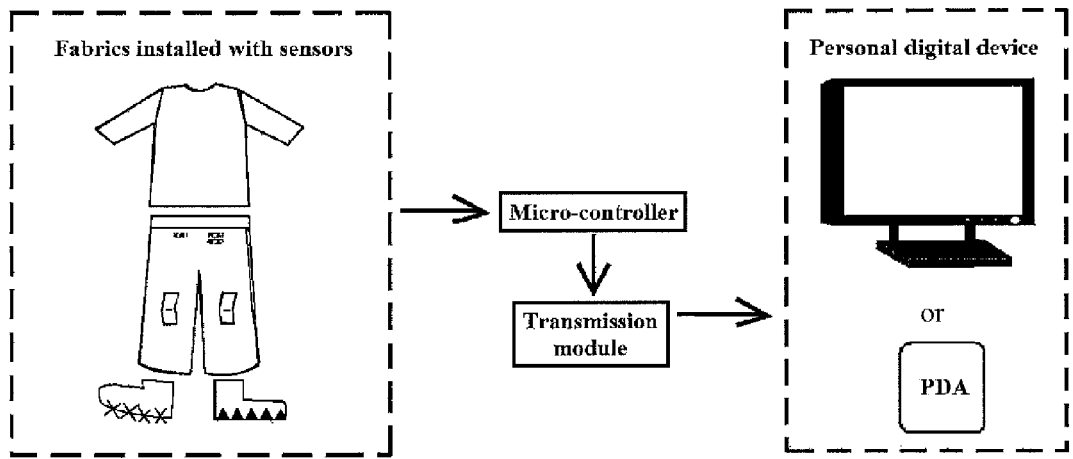
FIG. 1 illustrates a block diagram of a gait analysis system using textile sensors in accordance with one embodiment of the present invention.

A system block diagram of one embodiment of the present invention is as shown in FIG. 1. A number of switches, pressure, tension sensors or sensors are installed in socks, clothes or pants, depending on the applications (refer to PCT/CN2008/001570 Cloth comprising separable sensitive area, PCT/CN2005/001520 Electronic switch, PCT/CN2008/001571 Fabric able to form electronic element, and PCT/CN2009/000118 sensing device patent application). The above sensor may comprise a conductive material digital sensor, for example metal materials (such as: iron), non-metallic materials (such as rubber, silicone, foam) and conductive carbon materials (such as: graphite). In addition, during the manufacturing process, other flexible materials (such as rubber, foam, gel, sponge, springs, cotton, Spandex, synthetic elastic fiber (lycra), SBR (Styrene Butadience Rubber), and foam-based materials) can be added to the fabric so as to enhance the flexibility. Theses textile sensors may be connected with an input end of a microcontroller with a guide line. Once sensing posture change, the sensor may generate an input digital signal to the microcontroller. A program processing modules in the microcontroller may then simultaneously analyze, display and store the digital signal from all sensors or raise alarm as necessary, or the communication module transmits the signal to other personal digital devices such as smart phone or computer, for analysis, display, storage or raise alarm.

A textile sensor may be connected to a physiological sensor, so that the textile sensor may sense external force and produce reaction when the wearer moves and the physiological sensor may also sense the physiological signals of the wearer. n particular, when the wearer doesn't move, for example, he just stands or lies and shows no change in posture and gait, the physiological sensor may sense a physiological signal of wearer and detect his state.

The microcontroller may also be connected with a camera, an accelerometer or a gyroscope, depending on applications. The cameras, accelerometers or gyroscopes may be set in clothes, shoes, socks, control boxes or cell phones, in order to increase the accuracy of sensing body movement.

Preferred Embodiment 1

Figure 2:
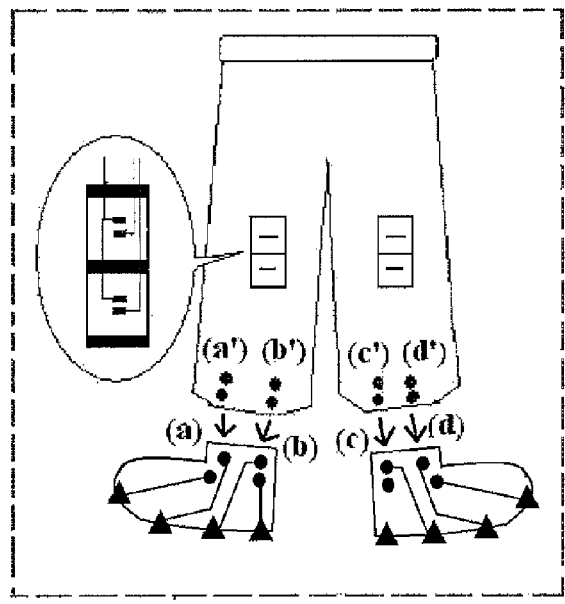
FIG. 2 illustrates a sensor block diagram of first preferred embodiment of a gait analysis system using textile sensors in accordance with one embodiment of the present invention.

As shown in FIG. 2, a sensor block diagram of a first preferred embodiment of the present invention may have four digital sensors respectively below socks of two soles of feet. When the external force is greater than a threshold value (e.g., 200 grams), the output value will change from the logical "1" to "0."

FIG. 3A shows a location plan of sensors in socks, and FIG. 3B shows a relative location plan of sensors in socks, where (12) corresponds to the heel of foot, (11) corresponds to foot side, (10) corresponds to the metatarsal and (9) corresponds to the big toe. Furthermore, to obtain more accurate gait information, two digital tension sensors may be installed in pants in areas above the knee caps and switch the output local state respectively at the flexion angles of 45° and 60°. FIG. 4A illustrates a plan of tension sensor being installed in pants. The angle of 60° is chosen as shown in FIG. 4B. A small angle sensor and a large angle sensor may be installed around the position of a knee, in which the small angle sensor may change an output state within a range of the knee's bending for 30 to 50°, preferably chosen as 40°; and the large scale angle sensor will change an output state within a range of the knee's bending for 60 to 100°, preferably chosen as 60°.

For a normal healthy person who is walking forward, the logical state sequence diagrams output by various digital sensors are as shown in FIG. 5, where sensors 1 to 4 are tension sensors and sensors 5 to 12 are pressure sensors. In FIG. 5, among sensors being installed to two legs, sensor 3 switches the first (right knee 45°) from "0" to "1"; meanwhile, the right leg is starting to raise and thus four sensors on the right foot are lift off successively (sensors 12 to 9 switch from logical "0" to "1"), the sensors on the left foot fall to the ground successively (sensors 8 to 5 switch from logical "1" to "0"). Then, the right leg lifts higher and results in the switch of sensor 4 (right knee 60°) from "0" to "1", the right foot is lift off completely (sensors 9 to 12 all demonstrate as "1"), and the left foot sole falls to the ground completely (sensors 5 to 8 all demonstrate as "0") while the left knee is straight (sensors 1 to 2 demonstrate as "0"). Next, the right leg is starting to fall and the right foot falls to the ground. Sensors 12 to 9 successively switch from "1" to "0" and meanwhile the left leg is starting to lift and the left foot is lift off and thus sensors 8 to 5 successively switch from "0" to "1". Meanwhile, as the left knee is starting to lift, sensors 1 and 2 switches from "0" to "1" and so on alternately. Embodiments of the present invention can then obtain the gait sequence diagram as illustrated in FIG. 5. The sequence diagram is analyzed as follows.

Figure 6:
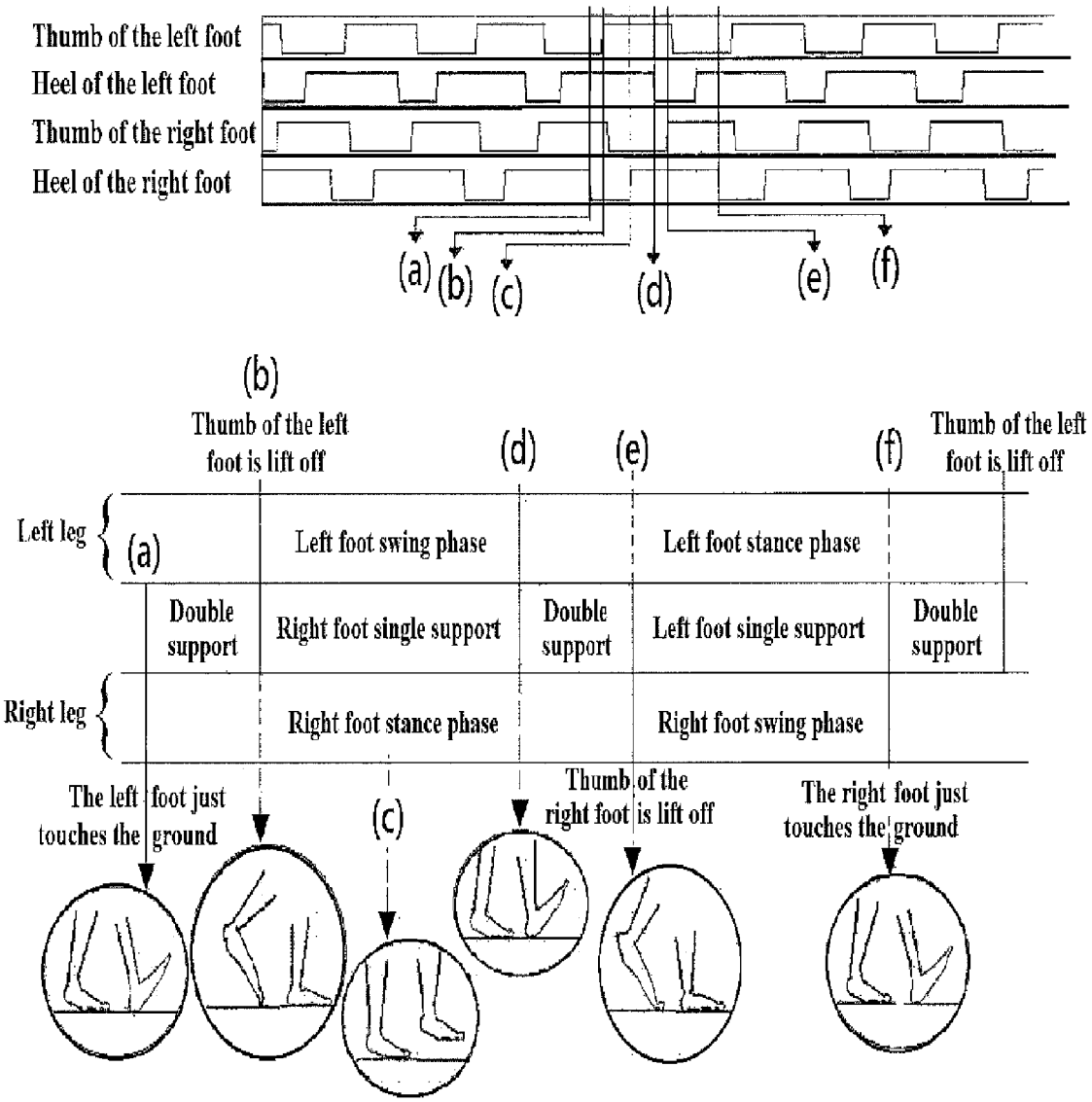
FIG. 6 illustrates a diagram of the first four phases in analysis of gait phase in accordance with one embodiment of the present invention.

The timing of gait is generally divided into seven phases, namely, loading response, mid-stance, terminal stance, pre-swing, initial swing, mid-swing and terminal swing, with the right heel's touching the ground as a starting point. The first four phases are collectively known as the stance phase. For the stance phase, embodiments of the present invention may complete with digital sensors installed on the toes and heels of both feet (sensors 5, 8, 9, 12), as shown in FIG. 6. Take (a) and (f) as the initial contact of the right foot, (b) as the left toe tip being lift off, (c) as the right heel being lift off, (d) as the left heel touching the ground and (e) as the left toe tip touching the ground. As sensed by sensors 5, 8, 9 and 12, (a) to (b) demonstrates loading response; (b) to (c) is the mid-stance; (c) to (d) is the terminal stance; (d) to (e) is the pre-swing; and (e) to (f) is the swing phase (see details in the next paragraph). The time of the first four phases as shown in FIG. 6 is successively 0.09, 0.23, 0.20, and 0.62 second. Meanwhile, the time required by double support, stance phase and swing phase of each foot and their respective proportion in the entire pace can be obtained.

Figure 7:
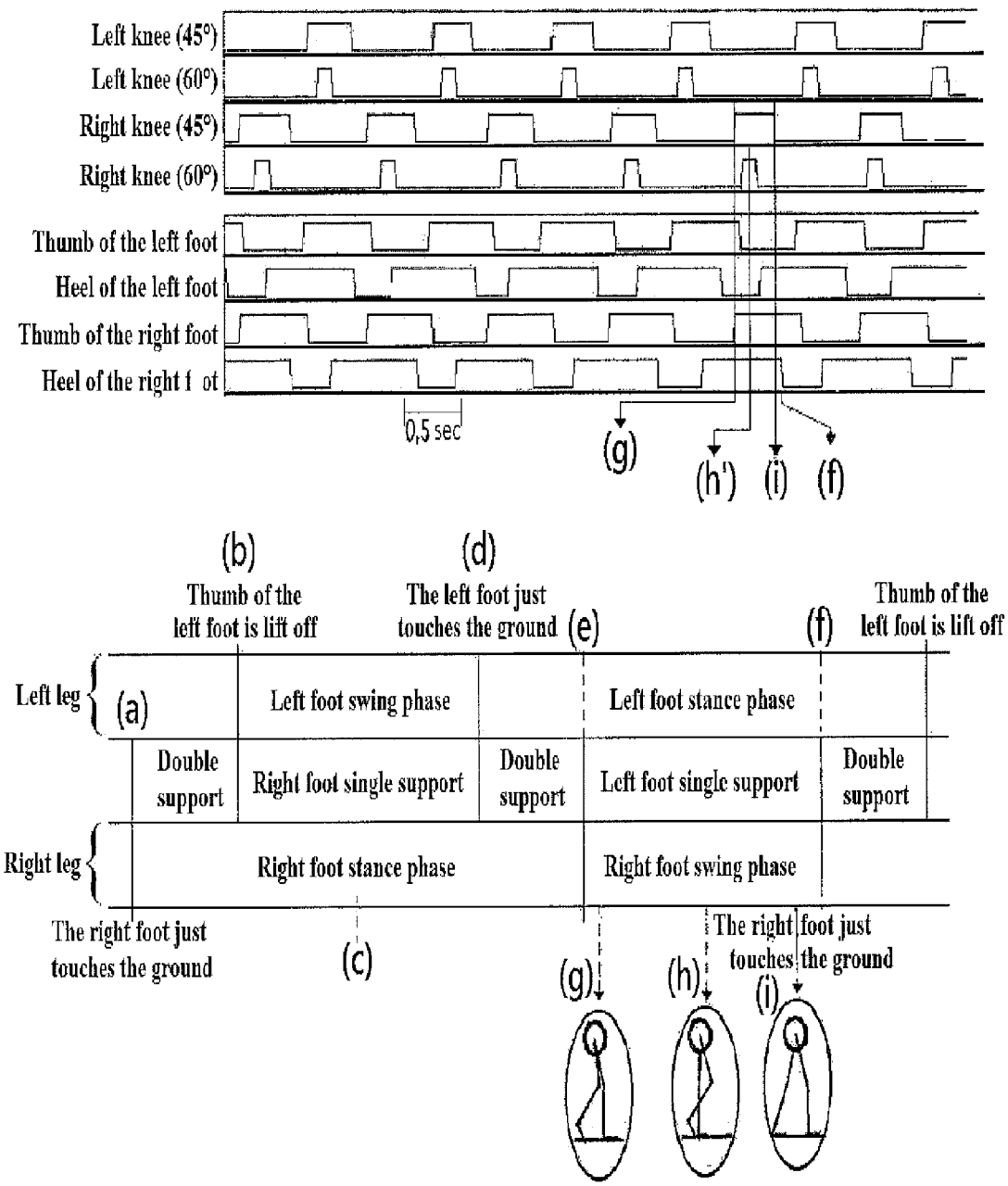
FIG. 7 illustrates a diagram of the last three phases in analysis of gait phase in accordance with one embodiment of the present invention.

The last three phases are known as the swing phase. For the last three phases, embodiments of the present invention may complete with four tension digital sensors installed on the knees of both feet (sensors 1, 2, 3, 4), as shown in FIG. 7. From an academic speaking, the initial swing should start from the right foot's being lift of the ground (g) and end at the most bending point (h) of the right knee. When a normal person lifts off his right foot (g), namely, the thumb of the right foot changes from "0" to "1", the bending angle of the right knee is 45° and sensors on the foot may sense the angle of the knee joint. The swing direction of the left arm and the swing change of the right foot are synchronous, namely, when the right foot swings forward, the left hand also swings back to front, the right foot changes from heel to toe and moves forward and the left arm swings front to back, namely, when the thumb of the right foot is lift off the ground, the right hand swings to the rear and the left hand swings to the front and when the right foot swings forward after lifting off the ground, the left hand also swings forward. Hence, the movements of hands, feet and joints and the body demonstrate corresponding change. So signal of a position may be used for sensing changes in other parts of the body as human body is an entire system. On the premise of balanced gravity, another part will move backward when a part moves forward so as to achieve dynamic balance. Thus, sensors in socks or those between socks and shoes or insoles may be used for sensing the changes in other joints. Where the left hand and left foot move simultaneously, the time and frequency of changes in gravity will be different from the ordinary ones and the normal and abnormal behaviors can thus be differentiated. In addition, changes in hands and feet while walking backward and going upstairs and upstairs are regular. Similarly, the signal change of another part may be observed from signal change of other parts. In embodiments of the present invention, it is replaced with the middle (h') of the right knee 60° tension sensor (sensor 4) when the output is "1". As sensed by sensors 1, 2, 3 and 4, (g) to (h') is initial swing; (h') to (i) is mid-swing (in which "i" is the point where the 45° sensor switches from "1" to "0"), and (i) to (f) is terminal swing. The time of the last three phases as shown in FIG. 7 is successively 0.12, 0.21, and 0.09 second. Meanwhile, we can learn the state of the knee joint or hip joint according to the sensor signal of the left and right feet. For example, the most bending point (h) of the right knee may be replaced by the time mid-point when sensors being installed to the left foot thumb and sole of foot are on the ground, namely, when the left foot is placed on the ground and the right leg knee is the most bending, the person achieves dynamic balance and the left hand and right hand swing symmetrically. Therefore, the movement of hands may be sensed by the sock sensors and sock sensors could evaluate the behavior of a person. Adding knee sensor, the results could be more accurate. We could predict the changes of angles of the hip or knee joint with sensors being installed on foot and the posture changes of feet according to the results of hip or knee joint sensors. Similarly, we could predict the changes in angles of the elbow or armpit joints when a person is walking or doing exercise with sensors being installed on foot and measure the changes in arms and predict the posture changes of feet according to the results of changes in angles of the elbow or armpit joints. Such correlation is more obvious when the user is walking at high speed.

Figure 8A:
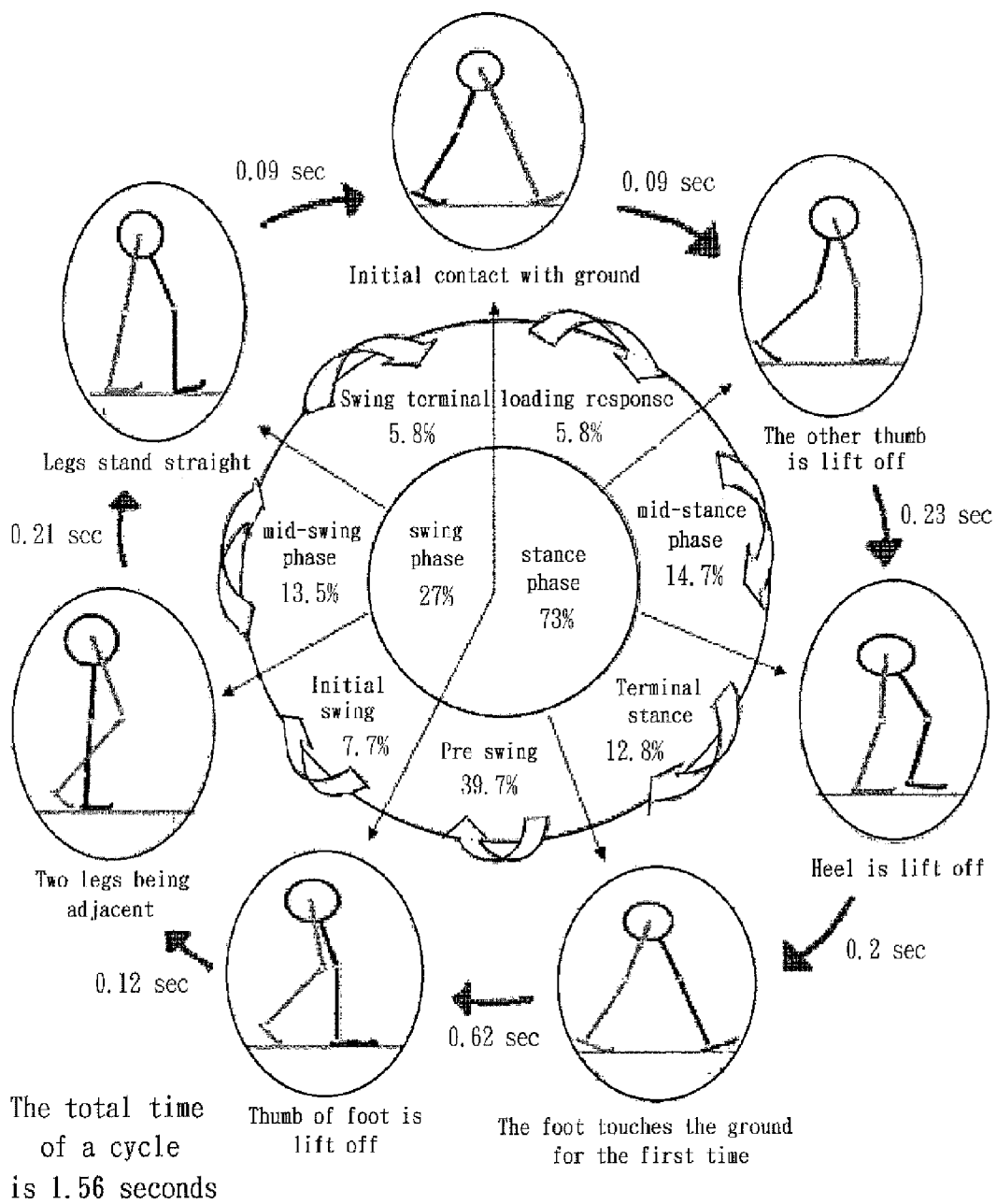
FIG. 8A illustrates a gait analysis diagram after completion in accordance with one embodiment of the present invention.

FIG. 8A illustrates a gait analysis diagram after completion of integration between the stance phase and the swing phase.

Figure 8B:
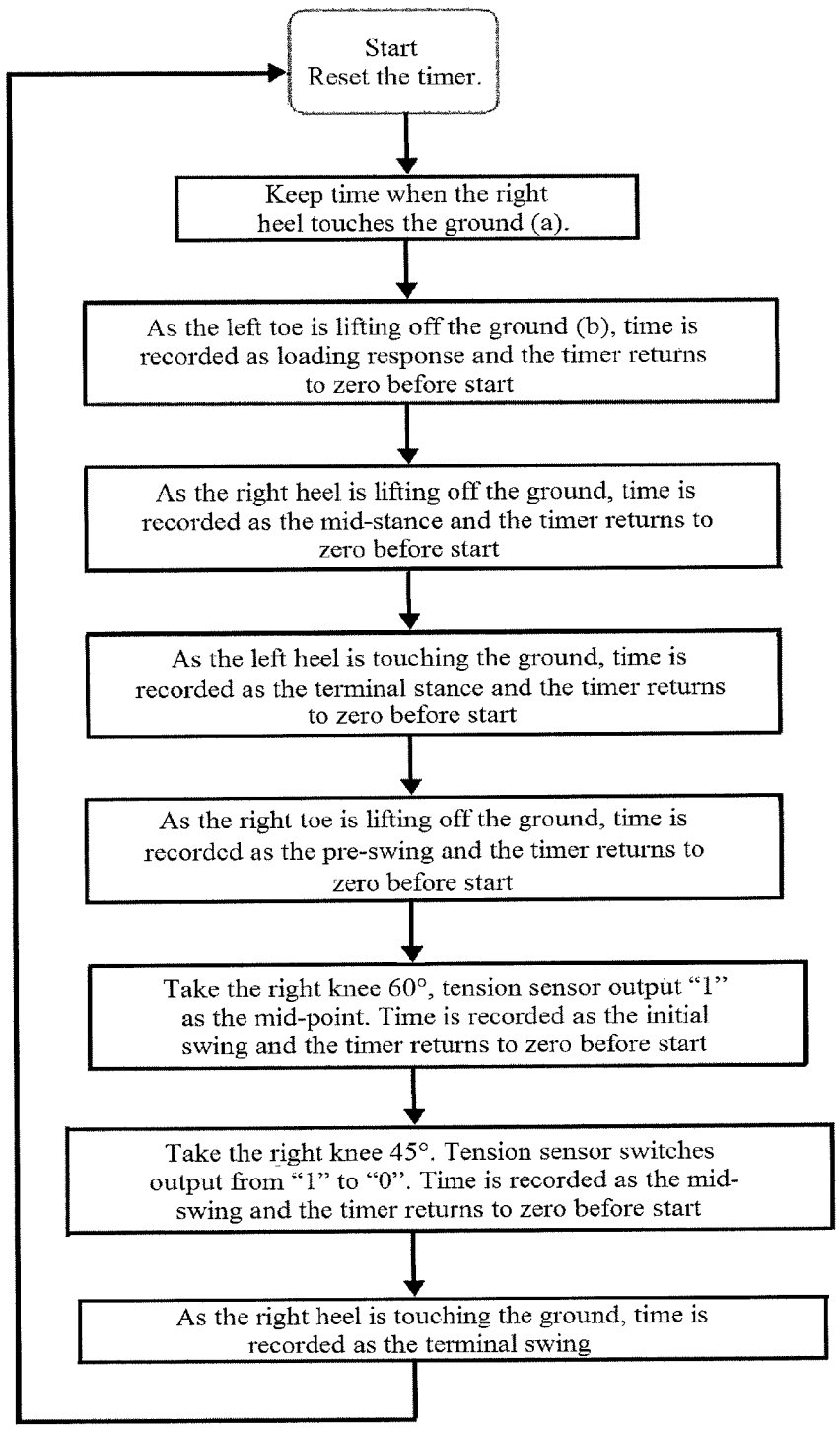
FIG. 8B illustrates a method flow chart of phase of gait in accordance with one embodiment of the present invention.

Based on the above, the microcontroller reads the logical state of each sensor at the sampling rate of 100 times per second. Thus, sufficient high temporal resolution can be used for measuring the time occupied in each gait phase, where all gait parameters and proportion can be presented. Take the right foot as an example, the flowchart of method is as shown in FIG. 8B. The same method applies to the left foot.

First, the timer will reset at the beginning;

Keep time when the right heel touches the ground (A);

As the left toe is lifting off the ground (b), time is recorded as loading response and the timer then returns to zero before start;

As the right heel is lifting off the ground, time is recorded as the mid-stance and the timer then returns to zero before start;

As the left heel is touching the ground, time is recorded as the terminal stance and the timer then returns to zero before start;

As the right toe is lifting off the ground, time is recorded as the pre-swing and the timer then returns to zero before start;

Take the right knee 60°, tension sensor output "1" as the mid-point. Time is recorded as the initial swing and the timer then returns to zero before start;

Take the right knee 45°. Tension sensor output switches from "1" to "0". Time is recorded as the mid-swing and the timer then returns to zero before start;

As the right heel is touching the ground, time is recorded as the terminal swing;

Then repeat the whole process.

The cycle of each phase of different steps of the same person may differ to some extent. Embodiments of the present invention may continuously record the cycle of all phases of each step in several minutes, calculate the average value and standard deviation of each parameter and meanwhile obtain the average value and average value and standard deviation of double support, stance phase and swing phase. Too great standard deviation of a person might represent that the person may have injuries on motor function. Though t his is a very important indicator, it could be completed through simple operation at very low cost by using embodiments of the present invention. In addition, the microcontroller may also be used for predicting the gait of the next step according to the current gait change information. If gait of two adjacent steps changes dramatically, it might indicate that the balance sense of the user is poor or the pavement is uneven, such as on a treadmill or on the bridge, or in case that the leg is injured or shoes are improper and so on. Under normal circumstances, gait of both feet should demonstrate periodic changes. Otherwise, the user might suffer from fall or other emergency situation. Embodiments of the present invention then can raise an alarm.

Analysis of Temporal Parameters

Figure 9:
FIG. 9 illustrates a diagram used for analysis of temporal parameters in accordance with one embodiment of the present invention.

Acoustic wave and RF (radio waves or radar systems) are applied in the transmitting and receiving system in socks. After the left sock transmits an electromagnetic wave, the right sock reflects the electromagnetic wave back to the left sock or directly receives the electromagnetic wave and hence obtains three important correlative time parameters, namely, the stride length, cadence and walking speed. With the sequence diagram, we can easily calculate the cadence. Using GPS (Global Positioning System), Sonic RF (radio infinite) systems or radar systems, stride length can be obtained by measuring the actual distance a user walks and divide by the number of steps or measured by the user himself. Otherwise, set in accordance with the average stride length found from the statistical data according to the human height or length of leg. The walking speed is obtained by multiplying the cadence by the stride length. First, use GPS (Global Positioning System) and RF (radio infinite) system, have the user walk freely for 10 meters and obtain the stride length. The user walks for 16 steps and thus the stride length is 10/16=0.625 meters. Then measure the number of steps according to the sequence diagram, as shown in FIG. 9. The time spent for the right heel's touching the ground for 5 times is 5.27 seconds, and thus, the cadence is 60*2*(5/5.27)=113.8 times/min (as both feet walk for one step before the right heel' touching the ground each time, 60*2 used to calculate the cadence). The walking speed is obtained by multiplying the stride length by the cadence, namely, 0.625*113.8=71.125 m/min (change to m/sec). One stride length equals to the step length of two steps. Have both feet walk for one step separately. Use sound detector or light, namely, electromagnetic waves to measure the parameters of both feet.

Center of Pressure (COP) and Center of Mass Analysis

Gait sequence diagram can clearly illustrate the switching sequence of sensors. However, for analyst who needs to analyze large amount of gait analysis information, it is difficult to read the sequence diagram. Therefore, embodiments of specifically defined the left or right foot Central of pressure (COP) and Center of Mass, namely the analysis method of center of gravity so that the analyst can quickly and easily analyze large amount of gait information. Dynamic changes in the centre of pressure (COP) of the user's left or right foot can be obtained in accordance with the center of pressure (COP); and changes of the whole body as a point on the ground can be observed in accordance with the center of mass (COM).

Figure 10A:
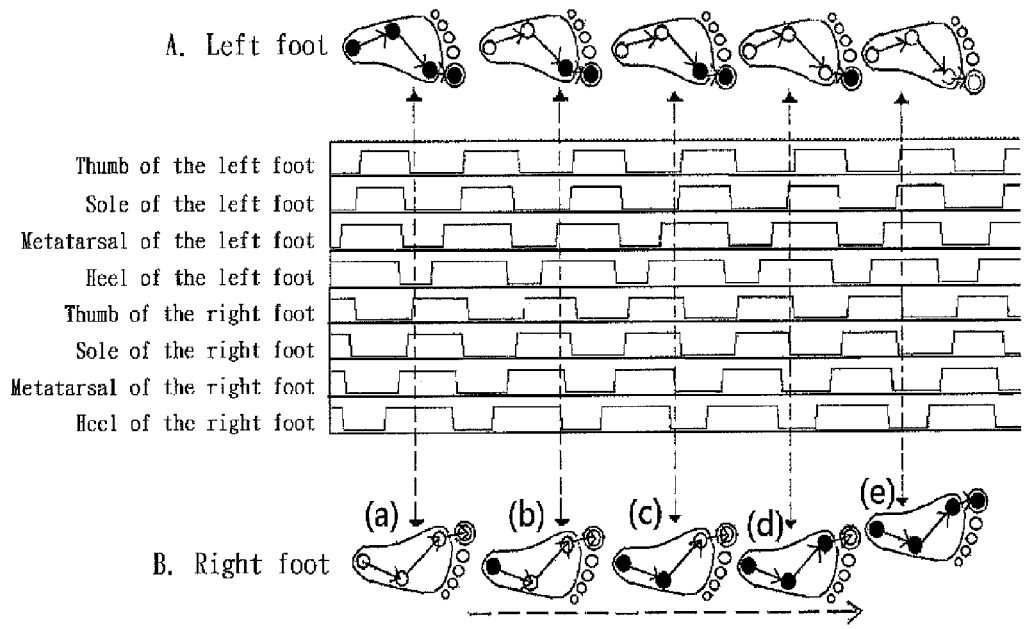
FIG. 10A illustrates an analysis chart about the pressure center in normal walking.
Figure 10B:
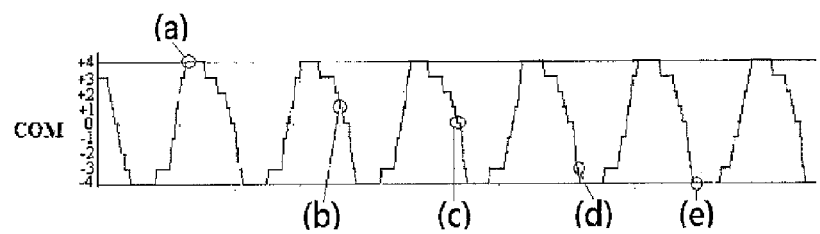
FIG. 10B illustrates an analysis chart about the mass center in normal walking.

The sequence diagram generated by digital sensors installed to both feet is as shown in FIG. 10A, in which, (a) shows that the four parts of the left foot are all on the ground while the four parts of the right foot are all off the ground, the following (b) shows that half of the left foot is off the ground with only the tiptoe and arch on the ground; comparing with (b), the following (c) has one more metatarsal of the right foot on the ground. The gait stability of a person can be observed from the changes in center of pressure, for example: even if the user does not move with both feet touching the ground, the center of pressure will still change over time and we can see the user's sense of balance and ability to control feet with brain. When the user stands on one foot, the center of pressure (COP) indicates the body weight. Embodiments of the present invention defines the sensor signal when the left foot is on the ground as positive signal and the sensor signal when the right foot is on the ground as negative signal. Sum of these two roughly refers to the center of mass of human body. Whether the center of gravity is inclined left or right, the FIG. 10B and (a), (b), (c), (d) and (e) in FIG. 10A all represent the gait of the same person. It can be seen from the analysis diagram of the center of pressure and center of mass (gravity) that when the left foot is completely on the ground while the right foot is completely lift off, the sum of both is +4, indicating that the center of mass of the body is inclined left. When both feet are completely touching the ground, the sum of both is 0, indicating that the center of mass of the body is in the middle. From changes in the center of mass over time as shown in the diagram, it can be analyzed whether the gait of the person is normal and regular.

Figure 10C:
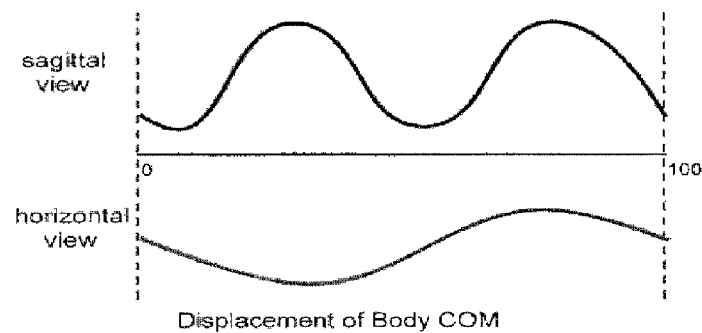
FIG. 10C illustrate a sagittal and horizontal view of the center of mass during walking

The changes in the center of mass can be divided into two dimensions, the horizontal view and the sagittal view, as shown in FIG. 10C, where the frequency of one curve may be multiple times of the other. Thus the changes of sagittal view can be estimated from that of horizontal view, and vice versa.

For example, after drinking wine, the user's changes in the center of mass (gravity) will become completely irregular. Similarly define the sensor signal when the left foot is on the ground as positive signal and the sensor signal when the right foot is on the ground as positive signal. The sum of both being dividend by 2 also indicates the center of mass of human body is inclined left or right. When the user does not move with both feet touching the ground, define the sensor signal when the left foot is on the ground as positive signal and the sensor signal when the right foot is on the ground as positive signal. The sum of both indicates the weight of human body. When analog or multi-level digital sensor is used, the center of mass (gravity) or the center of pressure could be more accurate. For example, among the digital sensors 0, 1, 2 and 3 of the third phase, 0 refers to 0 gram, 1 refers to 2000 grams, 2 refers to 4000 grams and 3 refers to 6000 grams. In another view, the center of pressure of user's left or right foot is obtained in accordance with the center of pressure COP. Where the center of pressure (COP) or center of mass (COM) is within the projection range of two feet on the ground, the user is stable. Where the center of pressure (COP) or center of mass (COM) is closer to the center of the projection range of two feet on the ground, the user is more stable and where the center of pressure (COP) or center of mass (COM) is closer to the edge region of the projection range of two feet, the user is more unstable and easier to fall. When the center of pressure (COP) or the center of mass (COM) stays in the edge region of the projection range of two feet on the ground for longer time, the user might be more unstable and easier to fall, especially when the center of pressure (COP) or the center of mass (COM) stays outside the edge region of the projection range of two feet on the ground. In case the position of the sensor below feet is independent coordinates but not the above mentioned left positive and right negative signals, and reaction of the left thumb is demonstrated as a coordinate value and reaction of the left heel is demonstrated as another coordinate value, and so on, the person's three-dimensional space and gravity changes, and three-dimensional spatial gait analysis and parameters can be obtained. In addition, we may measure if the central of gravity is within the range of two feet with accelerometers, gyroscopes or inclinometers. Where the central of gravity is outside the range of two feet for longer time or greater distance, the user is more unstable. Meanwhile, the accelerometers and gyroscopes may use the sensors below feet as reference points for correcting user's signal and reading the angle, signal of COP and COM or displacement.

Total Pressure, Posture State, and Total Movement Mass Analysis

The above-mentioned analysis of center of mass is helpful to alternating foot movements such as walking forward and backward and going upstairs and downstairs. However, it cannot be used for distinguishing some cases. For example, for movements with two feet move simultaneously such as keeping down or taking off jump, the center of mass is deemed as "0" and it cannot be distinguished. Therefore, embodiments of the present invention define total pressure, posture state, and total movement mass analysis method as follows:

Total pressure: The total number of sensor signal for foot pressure is all positive, regardless of positive or negative signal or signal of the left or right foot; greater value indicates that the contact area between feet and the ground is greater or the pressure of feet on the ground is greater. This is mainly used for distinguishing the pressure changes in user's contact with the ground, namely, pressure changes in both feet's contact with the ground. When the user stands on the ground and doesn't move, total pressure indicates the weight of human body Posture state: when changed of body sensors by external force, the posture state is the value of all the sensors of the user, indicating that there is force on the human body model which shows the change of the body posture or action. For example, when the sensor on the left side of the body senses external force and changes, it is set as positive and when the sensor on the right side of the body senses external force and changes, it is set as negative. Posture state is the sum of all sensor values. Where the value remains unchanged and be close to a stable value, it indicates that the left heel moves as the right arm swings and the right heel moves as the left arm swings. Where the value changes irregularly and be not close to a stable value "zero", it indicates that the user is unstable and likely to fall. When the user doesn't move, total pressure indicates the weight of human body.

Full-movement quality: for digital signal sum of the load carrying foot sensor and signal of all sensors being installed to the body (such as knee or elbow), all load carrying sensors are set as positive when they change. The higher the value indicates the user's more effective use of body muscle, namely, the whole body movement.

Gait Analysis of Running and Going Upstairs and Downstairs

Figure 10D:
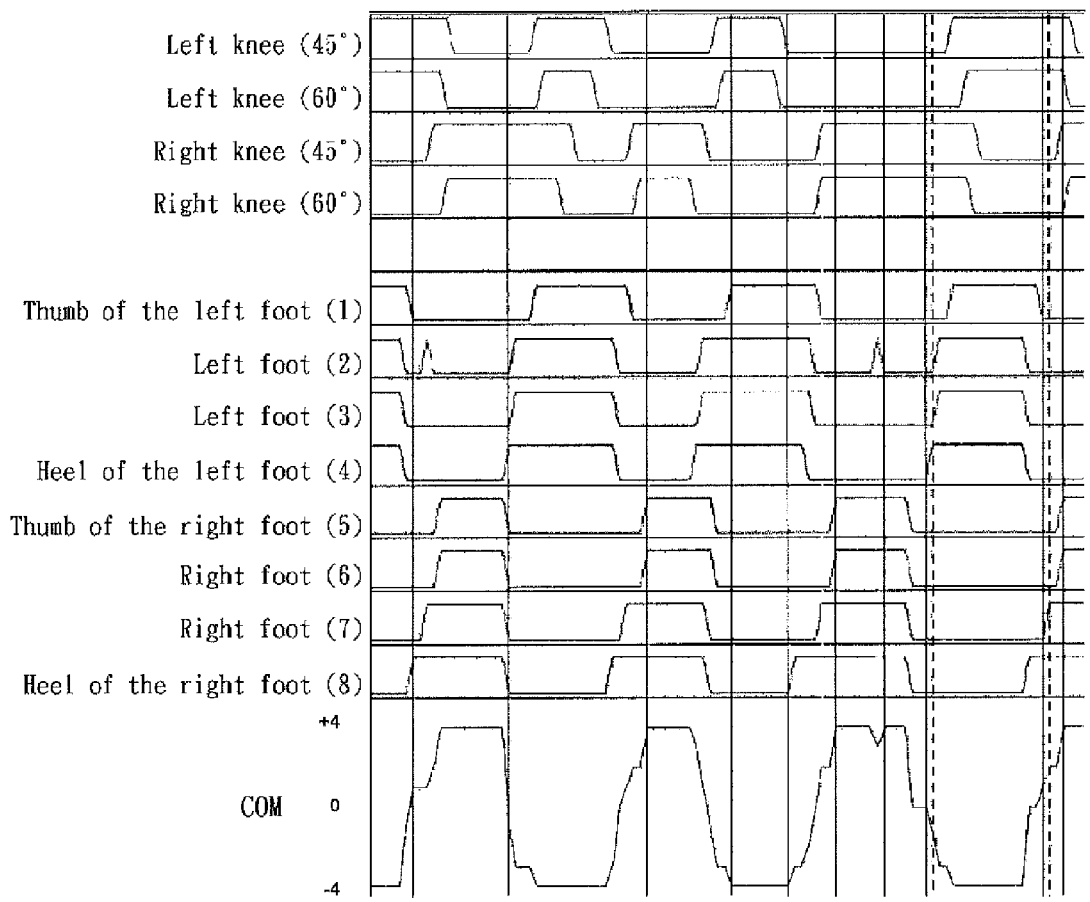
FIG. 10D illustrates an analysis chart about the pressure center and mass center during going upstairs.

COP and COM also exist in the process of going upstairs, running and going downstairs, as shown in diagrams 10D, 10E, and 10F. The COP and COM analysis diagram is as shown in FIG. 10D, where points a~h in FIG. 7 show the time points of gait analysis for going upstairs: point a refers to the signal when the right sole of foot is just stepped on the stair and also the starting point as defined in the analysis. It can be obviously seen from the vertical line drawing from the time point that, the bending angle of the right knee exceeds 60° while the left knee shows little bend; point b refers to the signal when the left sole is just lift off, and the bending angle of the left knee is just greater than 45° but less than 60°; point c refer to the signal when the bending angle of the left knee is just greater than 60°. Though, the bending angle of the right knee is still greater than 60°, it is in the state of reverting to small angle from large angle; time point d is the time point when the right knee just reverts to small angle. Point e refers to the signal when the left heel just steps on the stair. The bending angle of left knee at this time point is greater than 60° while the bending angle of the right knee is still less than 45°. Point f refers to the signal when the right heel is lifting off and the bending angle of knee is greater than 60°. Point g refers to the signal when the entire right sole is lifting off. Point h refers to the signal when the right sole steps on the stair for going upstairs. This is also the end point as defined in the analysis. The signal points a~h present the cycled gait analysis movement for going upstairs. In the analysis example, the right foot is taken as the focus of analysis. Time between point a and point b refers to the time when both feet support the body for the first time; time from point b to point e refers to the time when the right foot supports the body for the first time; time from point e to point g refers to the time when both feet support the body for the second time; and time from point g to point h refers to the time when the right foot swings in the air.

Figure 10E:
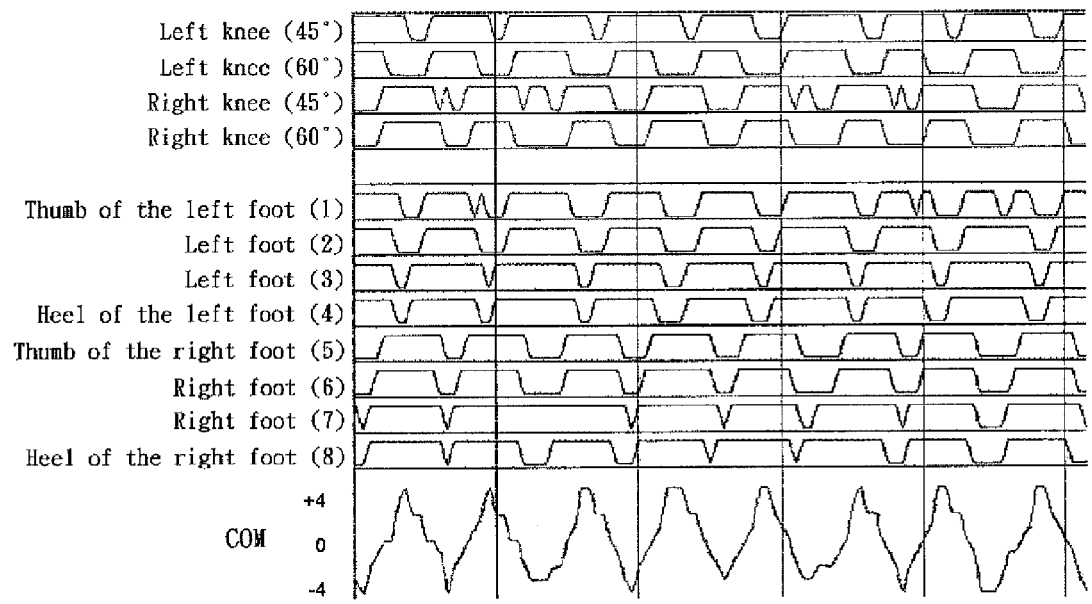
FIG. 10E illustrates an analysis chart about the pressure center and mass center during running

The COP and COM analysis diagram for running is as shown in FIG. 10E, where points a~e in FIG. 7 show the time points of gait analysis for running: point a refers to the signal when the right heel just steps on the ground and also the starting point as defined in the analysis. It can be obviously seen from the vertical line drawing from the time point that, the bending angle of the right knee at the time point is less than 45°, the left sole is lift off and the bending angle of the left knee is just greater than 60°; point b refers to the signal when the right tiptoe is just lift off, the bending angle of the right knee is just greater than 60° and that of the left knee is still 60° but in the state of reverting to bending angle less than 45°; point c refers to the signal when the left heel just steps on the ground, and the bending angle of the left knee is just greater than 45° but less than 60°; at this moment, the bending angle of the right knee is still greater than 60°, the time difference between point b and point c refers to the time when both feet still remain in the air as movement such as small leap might occur during the process of running; point d refers to the time point when the left tiptoe is just lift off, the bending angle of the left knee is just greater than 60° and that of the right knee is still 60° but in the state of reverting to bending angle less than 45°; and point e refers to the signal when the right heel just steps on the ground and this is also the end point as defined in the analysis. At this moment, the bending angle of the right knee is less than 45° and that of the left knee is still greater than 60°. The time difference between point d and point e refers to the time when both feet still remain in the air.

Figure 10F:
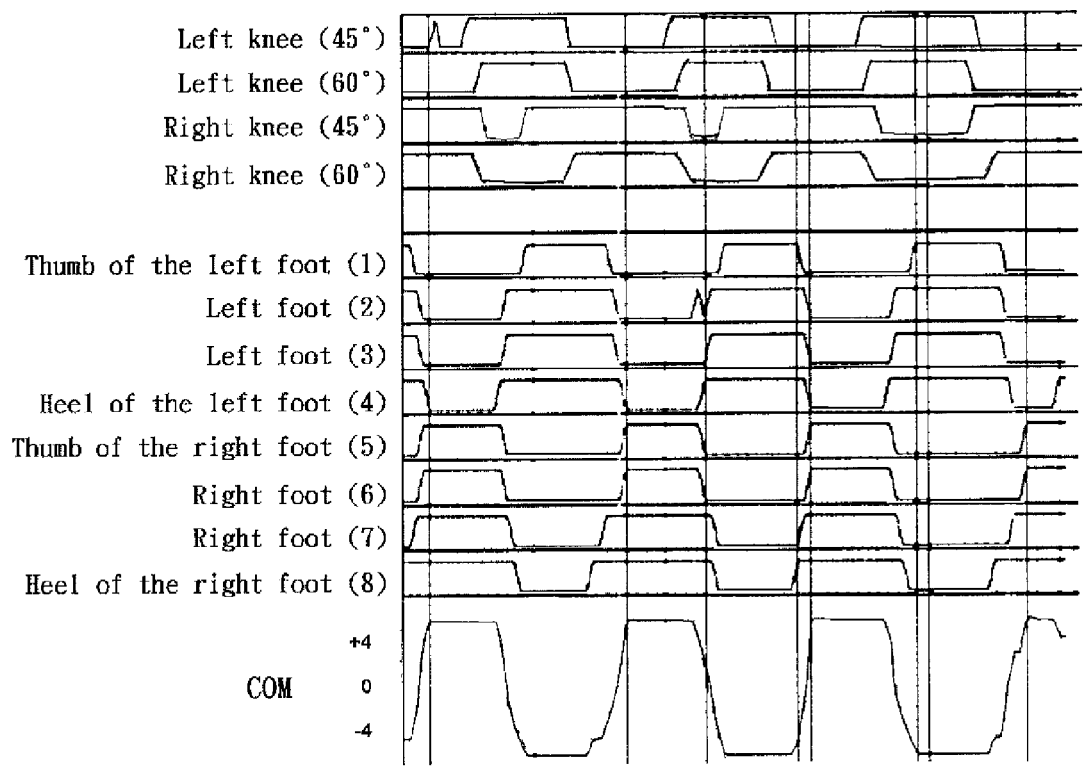
FIG. 10F illustrates an analysis chart about the pressure center and mass center during going downstairs in accordance with one embodiment of the present invention.

In FIG. 10F where the points a~f in FIG. 7 show the time points of gait analysis for going downstairs; point a refers to the signal when the right sole of foot just steps on the stair for going downstairs and also the starting point as defined in the analysis. It can be obviously seen from the vertical line drawing from the time point that, the bending angle of the right knee is less than 45° while the bending angle of the left knee is greater than 60°; point b refers to the signal when the right heel just steps on the stair for going downstairs and at this moment, the bending angle of the right knee is still less than 45° and that of the left knee is still greater than 60°; point c refers to the signal when the left tiptoe is lift off the stair while going downstairs, and at this moment the bending angle of the right knee is just greater than 60° and the right sole of foot is still on the stair; point d refers to the time point when the left tiptoe just steps on the stair for going downstairs, and at this moment the bending angle of the left knee is less than 45° and that of the right knee is greater than 60°; point e refers to the signal when the right tiptoe is just lift off the stair while going downstairs, and at this moment the bending angle of the right knee is greater than 60° and that of the left knee is still less than 45°; and point f refers to the signal when the right tiptoe just steps on the stair and this is also the end point as defined in the analysis.

Figure 11:
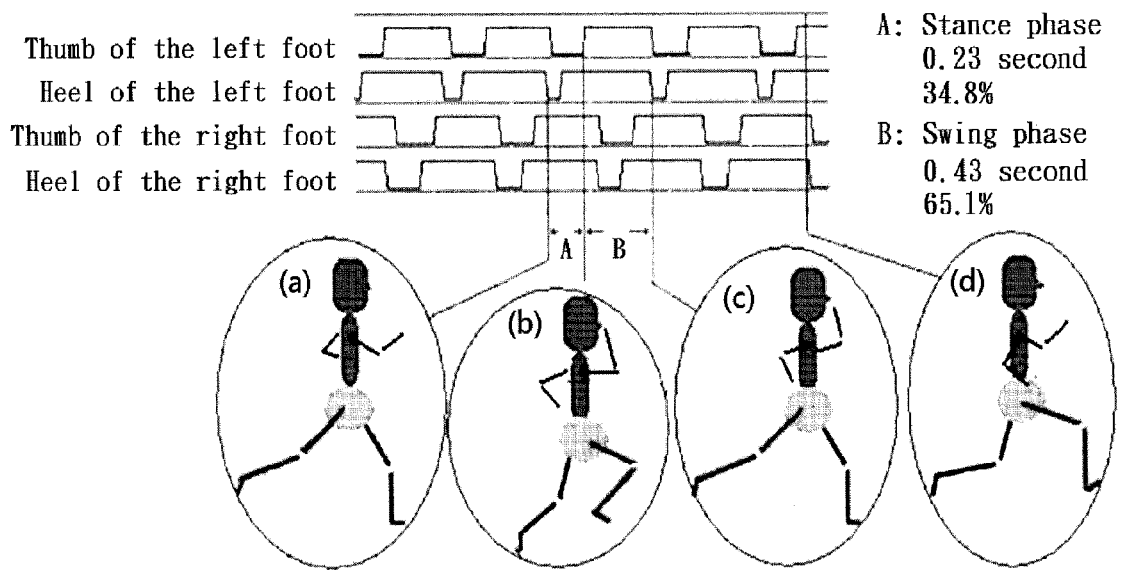
FIG. 11 illustrates a timing sequence diagram of gait during running in accordance with one embodiment of the present invention.

FIG. 11 illustrates the simplified gait during running. Compared with normal walking, it can be measured that the stance phase (a) is shortened, the swing phase (b) is increased and the time (c) when both feet touch the ground is very short and almost invisible in FIG. 11. In case sensors are installed to the position of arm in clothes, they can be used for further analyzing the user's exercise physiology. Under normal circumstances, the greater wing of hands indicates the faster movement of feet and they are synchronous: generally speaking, the left hand and the right foot are synchronous and meanwhile the right hand and the left foot are synchronous. When running faster, the bending angle of the elbow is greater. These may be used to assist gait analysis and analysis of the accuracy of exercise physiology and make it easier to determine the user's posture changes.

Figure 12:
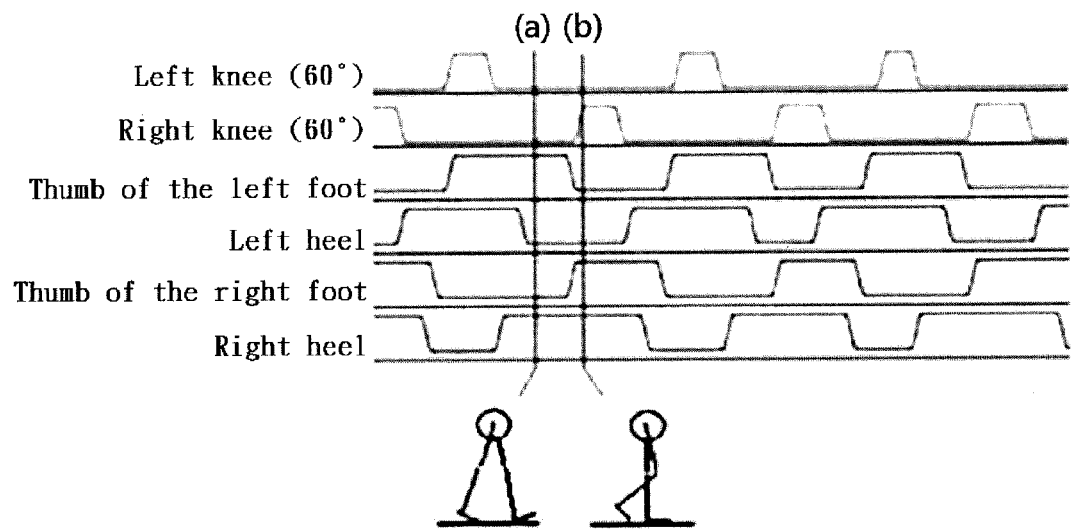
FIG. 12 illustrates a timing sequence diagram of gait during waking forward in accordance with one embodiment of the present invention.

FIG. 12 illustrates the simplified gait sequence diagram during waking forward.

Figure 13:
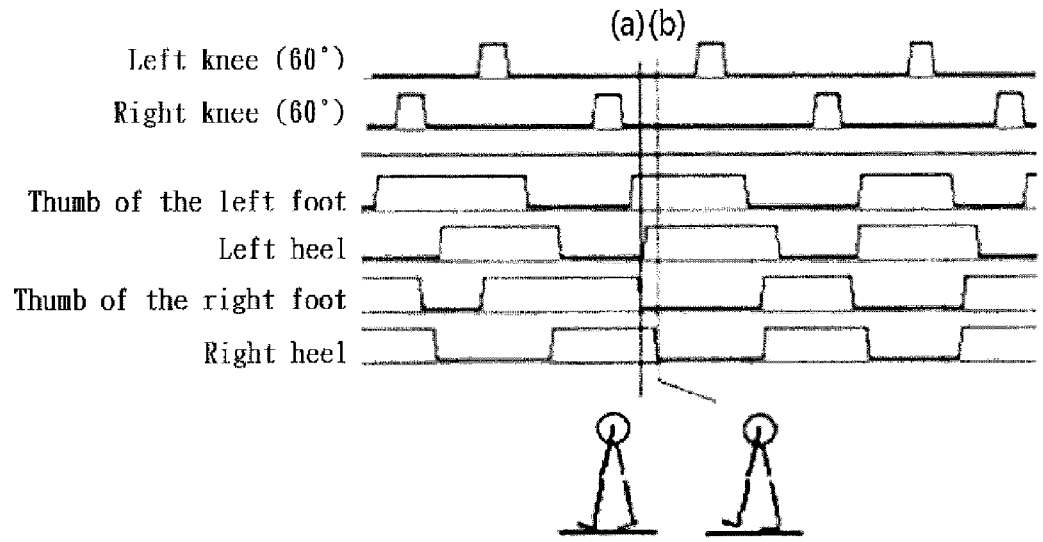
FIG. 13 illustrates a timing sequence diagram of gait during waking backward in accordance with one embodiment of the present invention.
Figure 14:
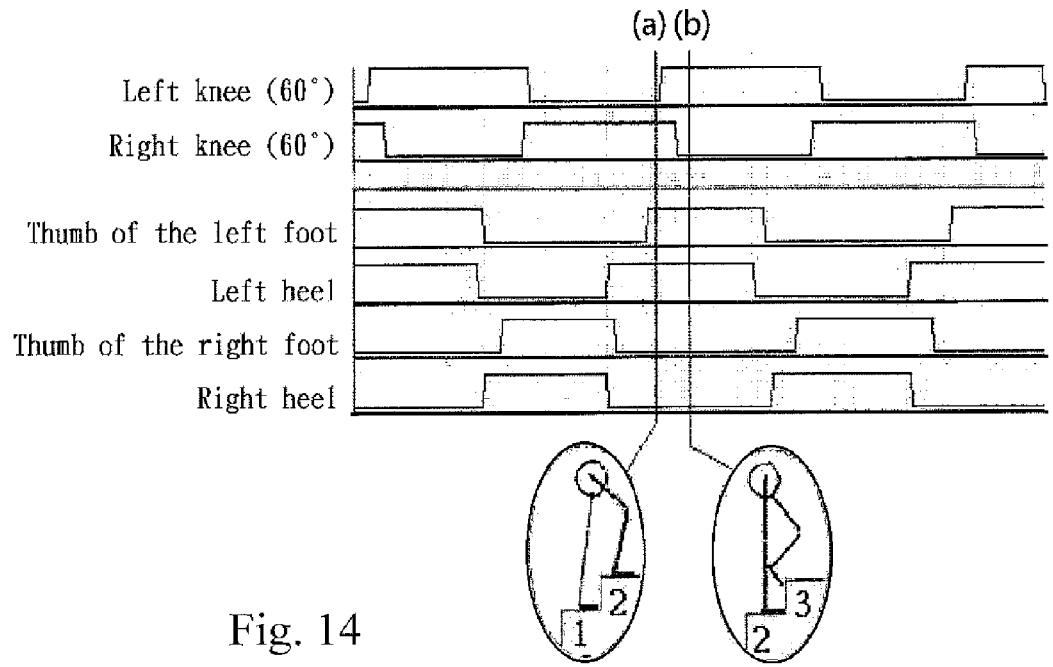
FIG. 14 illustrates a timing sequence diagram of gait during going upstairs in accordance with one embodiment of the present invention.

FIG. 13 illustrates the simplified gait sequence diagram during waking backward. Compared with normal walking, the phase change is reversible FIG. 14 illustrates the simplified gait sequence diagram during going upstairs. This is of significant differences compared to phases of normal walking. For example, when the left leg starts to go upstairs, the left knee is bent for more than 45° but not straight (refer to point (a) in FIG. 14) for the purpose of going upstairs. The right heel is on the next step ((b) in FIG. 13) and similarly the bending angle of the right knee is greater than 45°. On the other hand, the landing time difference between the heel and foot thumb is very small, as they almost touch the ground simultaneously. The bending time of knee is about twice as much as that of waking on flat ground.

Figure 15:
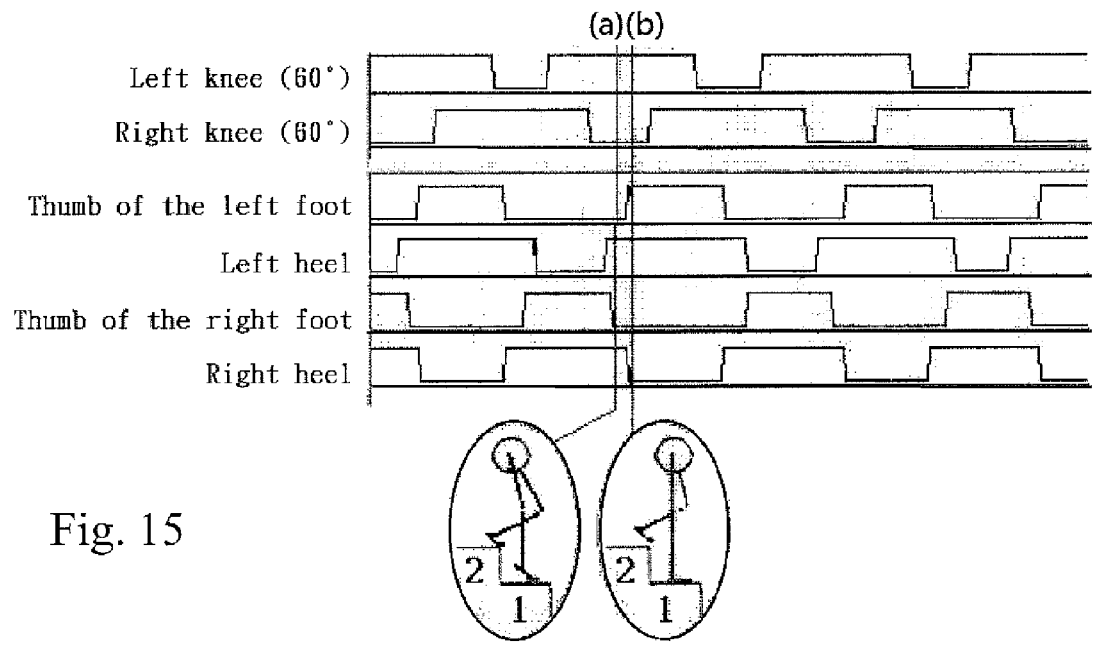
FIG. 15 illustrates a timing sequence diagram of gait during going downstairs in accordance with one embodiment of the present invention.

FIG. 15 illustrates the simplified gait sequence diagram during going downstairs. This is of significant differences compared to phases of normal walking. For example, in FIG. 15 step (a) shows the signal when the right foot tiptoe just steps on the next step after completion of the swing phase, rather than the heel's stepping on the ground first. The bending angle of the left knee is greater than 45°. It is also the left foot tiptoe that steps on the next step (b) first. In addition, we find that while going upstairs and downstairs, the time that sensor at the 60° position of knee generates "1" is longer than that during walking forward and backward. Thus, we can determine that the user is going upstairs or downstairs, or uphill or downhill if the time when the knee is bent for greater than 45° is longer than that of walking on flat ground. Moreover, with greater critical value, the knee sensor can detect greater inclination during going upstairs or downstairs, or uphill or downhill, instead of concluding a misjudgment. For example, on condition that the response time and lengths are same, the 60° sensor with greater inclination for going upstairs or downstairs, or uphill or downhill may last for the same time as that of 45° sensor. The 75° sensor may detect greater response to changes during going upstairs or downstairs, or uphill or downhill in the area of knees. Hence, by analyzing the gait signal, the style of shoes worn by the user at the moment can be sensed, such as: high heels, flat shoes, slippers, sports shoes, and so on.

Identify the movement of walking forward or backward, going upstairs or downstairs according to gait phase In conclusion, there are significant differences in gait phase sequences of walking forward, walking backward, going upstairs and going downstairs. According to embodiments of the present invention, the user's movement of walking forward or backward or going upstairs or downstairs can be identified by checking item A or item b in the following table. Of course, the principles of going uphill and downhill and going upstairs and downstairs are same. Thus, signal obtained by sensors can be used for assessing the situation on ground.

TABLE 1

The logic state table of walking forward, walking backward, going upstairs and going downstairs

|  | Walking forward | | Walking backward | | Going upstairs | | Going downstairs | |
| --- | --- | --- | --- | --- | --- | --- | --- | --- |
|  | A | B | A | B | A | B | A | B |
| (60°)Left knee (60°) | 0 | 0 | 0 | 0 | 0 | 1 | 1 | 1 |
| Left foot thumb | 1 | 0 | 1 | 1 | 1 | 1 | 0 | 1 |
| Left heel | 0 | 0 | 0 | 1 | 1 | 1 | 1 | 1 |
| (60°)Right knee (60°) | 0 | 1 | 0 | 0 | 1 | 0 | 0 | 0 |
| Right foot thumb | 0 | 1 | 0 | 0 | 0 | 0 | 0 | 0 |
| Right heel | 1 | 1 | 1 | 0 | 0 | 0 | 1 | 0 |

Of course, considering the various confounding factors, not phase sequences generated by all steps are the same as described in the above table. In embodiments of the present invention, more sensors may be installed in pants, socks or clothing so as to improve the correct rate of identification. For example, if two sensors are installed in the area of hip in pants, when two socks sensors, two sensors in the knee area of pants and two sensors in the hip area in pants are all demonstrated as "1", that means that the user is sitting with two legs hanging in the air as the chair height is greater than the length of leg. In summer, most users wear shorts. Thus, the sensors being installed in area of knee joint are replaced with those being installed in the thigh area in pants or those being installed in the hip joint area in pants for detecting the leg movement when a people is moving. Of course, the gait measuring accuracy could be higher if sensors are installed in all locations in pants.

Figure 16:
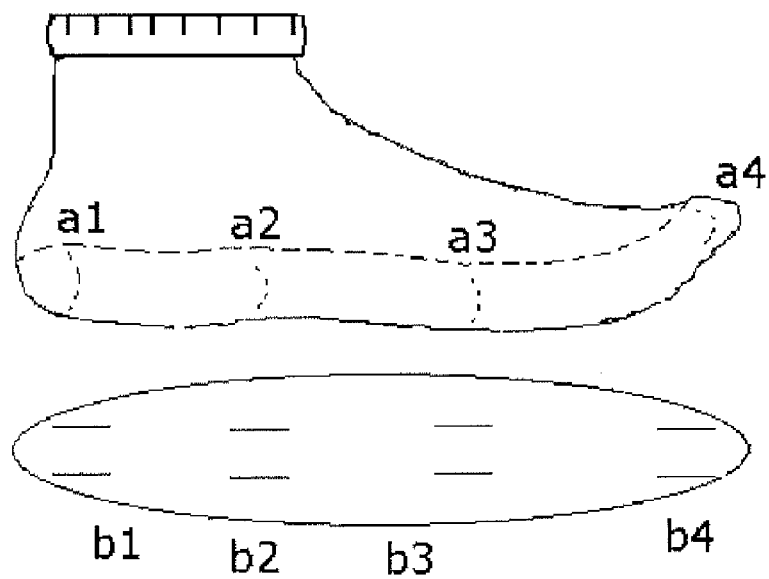
FIG. 16 illustrates a diagram of the first sock sensing system in accordance with one embodiment of the present invention.

As it is possible that sensors in socks cannot be connected to the controller in pants or cell phone, sensors in socks are combined with shoes or insoles, as shown in FIG. 16. Four conductive threads a1, a2, a3, and a4 are sewed on socks, and they are corresponding to conductive material b1, b2, b3 and b4 in shoes or insoles. When the heel contacts the ground, a1 connects both ends of b1 and switch the state "1" of b1 to "0". Moreover, microprocessors are installed to shoes or insoles for analyzing, displaying, storing or sending out signal.

So do the other sock. Wireless communication means such as RFID or Zigbee are used for information transmission. This may also realize interaction with microprocessors such as controller on clothes or cell phone and finally achieve interaction with external control system by means of wireless transmission.

Figure 17:
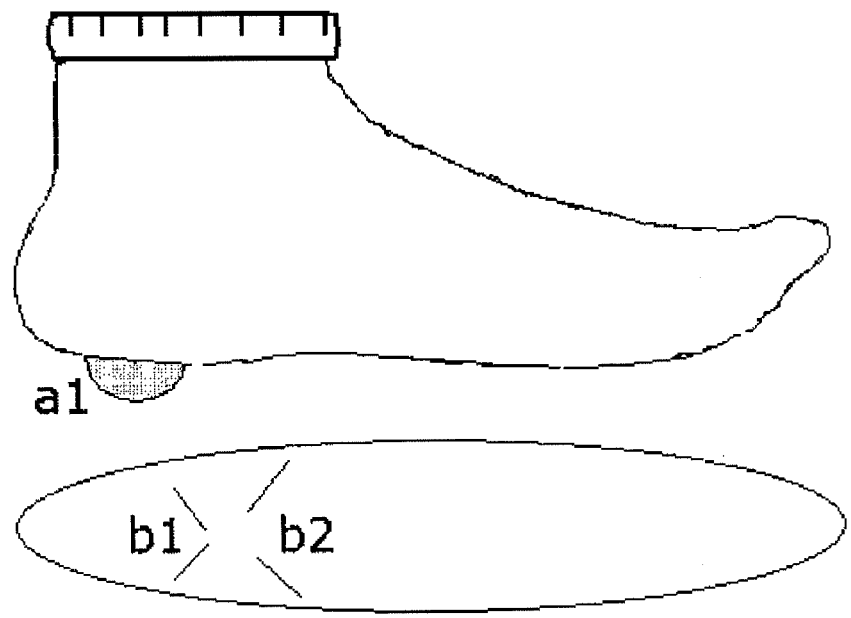
FIG. 17 illustrates a diagram of the second sock sensing system in accordance with one embodiment of the present invention.

Of course, sensors being installed in socks, shoes or insoles may also be multiple stage type, as shown in FIG. 17. There is a half spherical protruding conductive material in sock and there are two groups of concentric conductive wires b1, and b2 in the lining of corresponding shoe or insole. The wire space of b1 is less than of b2. Thus, when the heel presses downward, the conductive material of a1, such as conductive rubber or conductive metal sheet first conducts both end wires of b1; and when the heel further presses downward, a1 further conducts both end wires of b2. Thus there are two stages of pressure performance on the same point of heel, rather than the above mentioned single switch or single stage pressure sensor. Several multiple stage sensors may be installed in different locations in socks, shoes or insoles for sensing change of pressure (COP) in gait. Each point at the center of pressure (COP) presents different pressure changes. Thus when the center of mass (COM) is to be presented, the dynamic change in people's center of mass (COM) may be observed as each point doesn't simply present switch from "0" to "1" but show certain weighting and may better present dynamic changes in people's center of mass (COM) during walking. Total pressure, posture state, and total movement mass all show different multiple stage dynamic changes.

Figure 18:
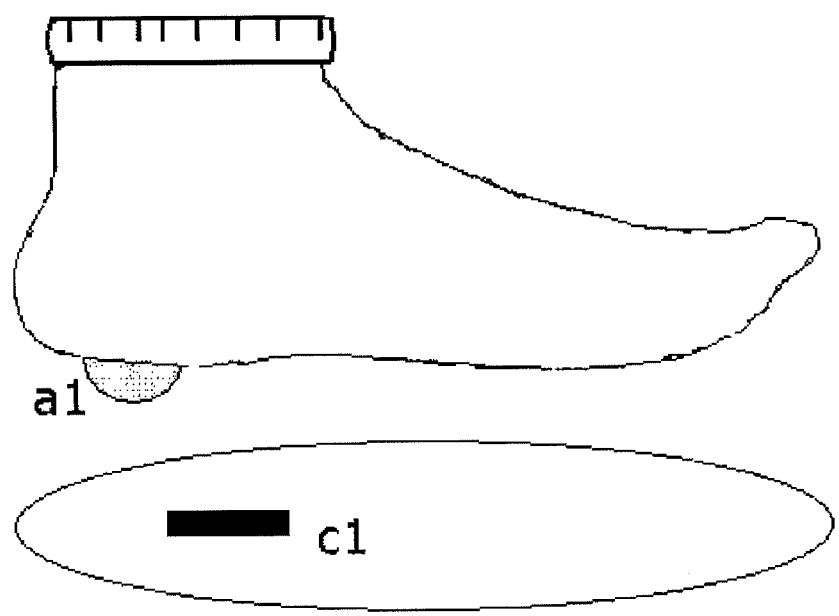
FIG. 18 illustrates a diagram of the third sock sensing system in accordance with one embodiment of the present invention.

To obtain more accurate analysis results, we can combine the two separate conductive wires of b1 and b2 with the socks conductive hemisphere a1 to form multiple stage pressure sensors. As shown in FIG. 18, replace b1 and b2 with variable resistor, piezoelectric material, variable capacitor or variable inductor c1 in shoes or insoles. c1 is installed in the lining of shoes or insoles, with one end being corresponding to the center of socks hemisphere to measure the resistance at both ends of the c1. The greater pressure indicates more contact between hemisphere a1 and c1, leading to decreased resistance at both ends of c1 as the gravity increases. It can also be measured when c1 is piezoelectric material or variable capacitor. The signal sensed by each sensor is analog signal. In short we split original socks sensor and install part of it in shoes or insoles, such as in shoes or inner part of insoles or socks; surface of socks and shoes or inner part of insoles; or inner part of socks and shoes or surface of insoles for sensing user's gait changes. Variable material or piezoelectric material as shown in FIG. 18 can also be set on socks. In addition, camera accelerometer or gyroscope may also be set on shoes so as to detect the accelerated speed and angular velocity of movement and make the detected information more accurate.

The following rules can be summarized from the phases of the various aforementioned gaits and such rules can also be used to identify gaits such as walking forward, walking backward, going upstairs and going downstairs.

Walking Forward:
1. In general, heel touches the ground first when we walk forward. Thus, the heel signal appears earlier than that of the tiptoe.
2. When the heel touches the ground, knee of the leg is bent for less than 45°.

Walking Backward:
1. In general, the tiptoe touches the ground first when we walk backward. Thus, the tiptoe signal appears earlier than that of the heel.
2. The signal when knee is bent for more than 60° is usually closer to signal of tiptoe.

Going Upstairs:
1. Before signal of the foot's touching the ground, signal representing that the knee of the leg is bent for more than 60° appears.
2. When signal of the foot's touching the ground appears, signal of the knee remains to be more than 60°.
3. The signal representing that the knee just turns to be straight appears during the period when the foot touches the ground.
4. Heel usually touches the ground first. Thus, signal of the heel appears earlier.

Going Downstairs:
1. As the tiptoe touches the ground first, the tiptoe signal appears earlier.
2. When the tiptoe signal appears, the knee signal of the leg is less than 45° bending.
3. The signal representing that the knee just turns to be bent for more than 60° appears during the period when the foot touches the ground.

In addition, heart rate, body temperature, sweat, blood oxygen, ECG, blood pressure, breathing and other physiological sensors can be installed to clothing and socks and connected with the textile sensors for sensing the physiological functions.

Also, though the gait analysis is different when users are using crutches, cart or stand, the changes in center of gravity and changes between the left and right feet can be estimated.

Preferred Embodiment 2

Figure 19A:
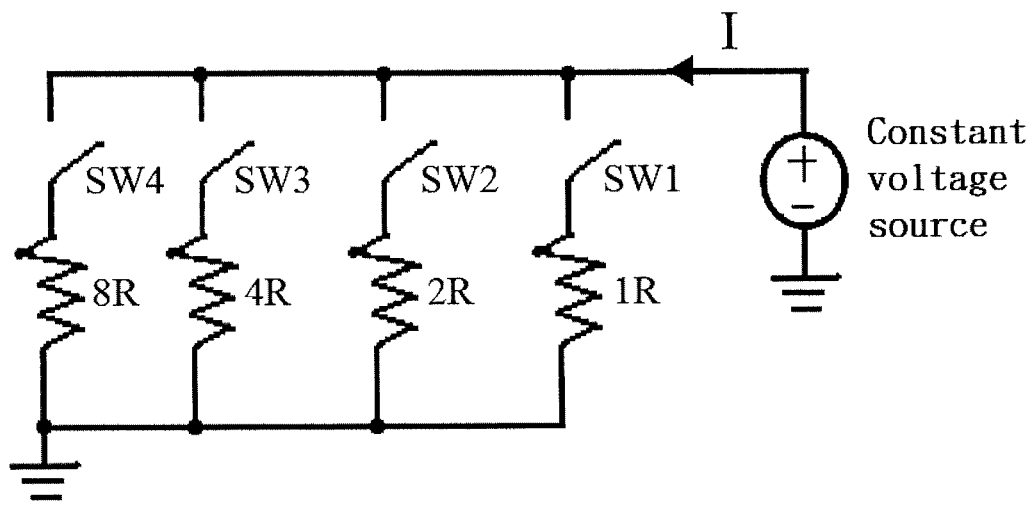
FIG. 19A illustrates a circuit diagram of installing a resistor next to the sensor and connecting in parallel.

To make fabrics used in embodiments of the present invention washable and comfortable as general fabrics, stainless steel wire which is flexible and washable is used in the invention to connect sensors and micro-controllers. That is, stainless steel wire is used as transmission line. Of course, other conductive material can also be used as transmission line for transmitting signals or current and use socks, clothing, or pants as the circuit board. Connect stainless steel wire and micro-controller or, socks, clothing and pants with common press buttons or snap buttons. For ensuring the comfort of clothing, there should not be too many stainless steel wires, press buttons or snap buttons. If multiple sensors are needed in practical application, embodiments of the present invention may have one electric resistor being installed separately beside each textile sensor at the resistance ratio of 2 and connect the resistors in series (FIG. 19B) or in parallel (FIG. 19A). This concept is similar to the binary code. As the circuit being shown in FIG. 19B, equivalent resistances formed by four sensors are 0, R, 2R, 3R, 4R, 5R . . . up to 15R, altogether 16 values. This may ensure that the equivalent resistors connected in series or in parallel are not the same no matter how the textile sensors switch. Thus after analog-digital conversion, the microcontrollers may distinguish the logical state of various textile sensors. This can significantly reduce the use of transmission lines and press buttons or snap buttons.

FIG. 19A demonstrates the measurement of the electric current output I, from which we can calculate the equivalent resistance of the four sensors. Similarly, FIG. 19B demonstrates the measurement of the voltage output V, from which we can calculate the equivalent resistance of the four sensors. In addition, if the above-mentioned resistors in FIG. 19A and FIG. 19B are changed to capacitors or inductors, in coordination with also changing the constant voltage source and the constant electric current source into an alternating current (AC) voltage source and an AC electric current source, we can read the equivalent capacitance or inductance of the four sensors based on the same principle.

Figure 19B:
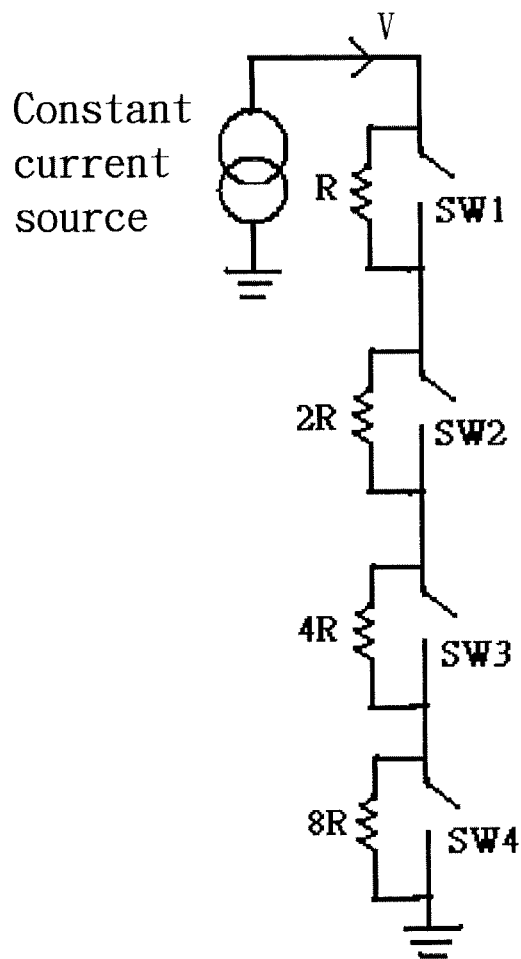
FIG. 19B illustrates a circuit diagram of installing a resistor next to the sensor and connecting in series.
Figure 19C:
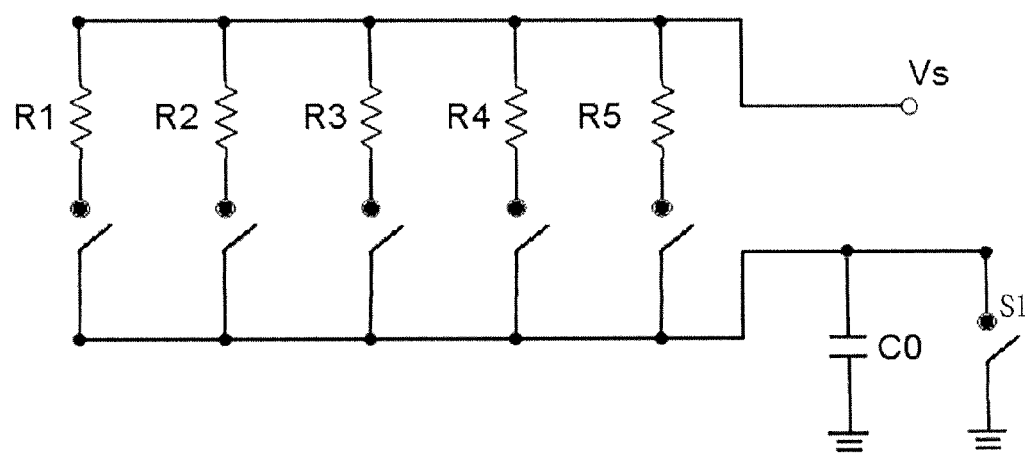
FIG. 19C illustrates a charging/discharging circuit to measure the Req of the resistors and switch network.
Figure 19D:
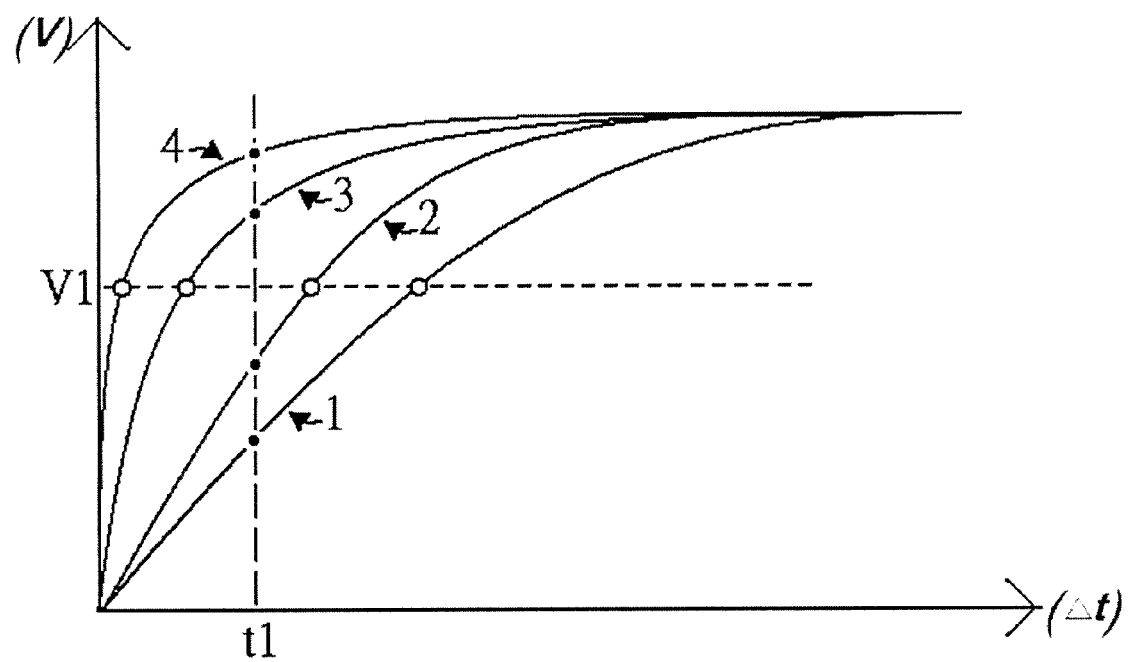
FIG. 19D illustrates charging curves by pressing different switches in accordance with one embodiment of the present invention.

Similarly, to read the equivalent resistance Req of the circuit in the multiple sensors in FIG. 19A or FIG. 19B, aside from the measured electric current output or the measured voltage output as shown in FIG. 19A or FIG. 19B, we can also connect in series a capacitor C to form the electric circuit as shown in FIG. 19C to charge the sensor circuit by pulse wave. There are two ways to read the Req: The first method is to set a threshold voltage Vth, and measuring the time t required to charge from (t=0) to Vth, using Vth=Vs (1−exp (t/Req*C)), to derive Req as shown in FIG. 19D; the second method is to set a fixed charging time dt to measure its voltage V, using V=Vs (1−exp (dt/Req*C)) to derive Req; the third method is to continuously capture the voltage of the capacitor C when charging starts, and obtaining its charging curve, for example, curve 1, curve 2 of FIG. 19D, etc., then we can use current digital signal processing technology (for example, a Butterworth low-pass filter) to reduce noise, and obtain the equivalent resistance Req by taking logarithm of the curve and then calculate its linear regression, and then we can learn the status of the sensor when pressure is being applied, at the same time obtaining the gait status. The above the three methods can also be used in combination, such as the second method and the third method.

After charging has been completed, the microcontroller will turn on the electronic switch S1 as shown in FIG. 19C, and let out the electric charge of C to the ground, enabling it to be ready to measure again. The benefit of connecting in series a capacitor C lies in the fact that when a capacitor and a resistor are combined into a low-pass filter, it inhibits the sensor from the bouncing that accompanies it during switching. Besides, with the operating speed of the microcontroller, it can accomplish several thousand times of charging and discharging in order to read the equivalent resistance Req to achieve a rapid, real-time gait detection. Besides, the microcontroller can carry out digital signal processing through firmware in order to suppress the noise interference caused by bouncing and electromagnetic interference.

Similarly, the electronic components that are connected in series or parallel to textile sensors may not only be in the form of resistors, capacitors, or inductors, but can also be other more complex components such as diodes. Assuming that we alter the SW1 in FIG. 19A to be connected in series to one diode instead of the original resistor R, allow the current to flow from left to right instead, alter the SW2 to be connected in series to one diode instead of the original resistor 2R, allow the current to flow from right to left instead, change the original voltage source to an AC voltage source; so when the power supply is a half cycle and SW1 is depressed and electrically conducted, only then will the current flow through SW1; Similarly, when the power supply is at negative half cycle and SW2 is depressed and electrically conducted, only then will current will flow through SW2. Thus, through the AC power and connecting to diodes in different directions, the processor will be able to segregate different sensors. Similarly, the textile sensors can have both amplifying and rectifying actions when connected to a transistor.

Similarly, the textile sensors can be connected to an op amp, such that the SW1 in FIG. 19A is altered to first connect to the input terminal of an op-amp with Schmidt trigger, then followed by the output terminal of the Schmidt trigger connecting to the resistor R, and SW2, SW3, SW4 also connecting to the Schmidt trigger in similar fashion, so we can reduce the interference of SW1 caused by bouncing using the Schmidt trigger, and also segregate different sensors through the resistors R, 2R, 4R, and 8R. Similarly, the above-mentioned electronic components can be accomplished using the method of integrated circuit (IC).

The method of textile sensors connecting to electronic components as described above can not only can be implemented independently but also in combination with others.

Besides stainless steel wire, silver wire, copper wire, conductive silicone and other conductive materials may also be used as transmission line. Similarly, the desired effect may be achieved through capacitor or inductor or resistor being connected in series or parallel. Meanwhile, if such electronic components being connected in series or in parallel are set below feet, they may stimulate growth and have a massage effect in walking.

Preferred Embodiment 3

Figure 20:
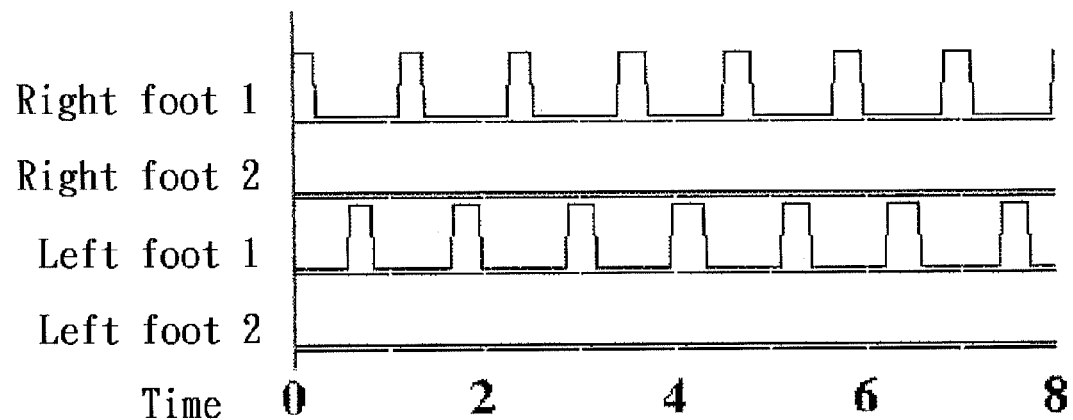
FIG. 20 illustrates a sequence diagram obtained from knight's walking in accordance with one embodiment of the present invention.
Figure 21:
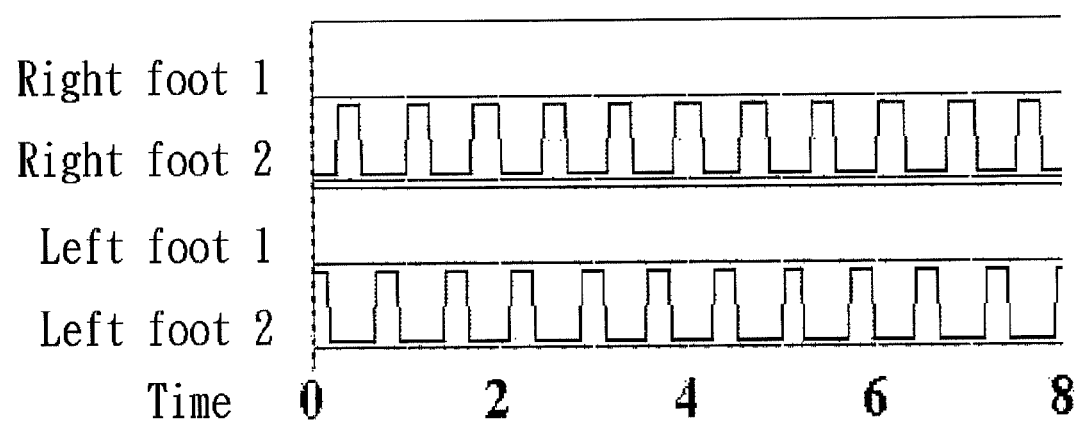
FIG. 21 illustrates a sequence diagram obtained from knight's riding a bicycle in accordance with one embodiment of the present invention.

In addition to gait analysis, embodiments of the present invention also can be applied to bicycle rider, for calculating the pedal turns. As the radius of tire is R, a circle is $2\pi R$ and hence the movement distance and speed can be estimated because the spent time can be learnt from the processor. For a bicycle rider, an embodiment of the present invention may install a 40° digital sensor and a 90° digital sensor on both knee joints. The sequence diagrams obtained during bicycle rider's walking and riding are as shown in FIG. 20 and FIG. 21, in which the right sensor No. 1 and left sensor No. 1 are 40° sensors and the right sensor No. 2 and left sensor No. 2 are 90° sensors. As the knee is not bent for more than 90° during walking, the two 90° digital sensors on knees as shown in FIG. 20 are displayed as "0" and only the 40° digital sensor may be switched over. While riding a bicycle, both knees are bent for at least 40° and the two 40° digital sensors on knees as shown in FIG. 21 are displayed as "0", and only the 90° digital sensor may be switched over. When riding a bicycle, the soles of feet are stepped on bike's foot pedals, the sensors are all in the "0" conducting state. Thus, response may only be available when sensors are installed in position of knee at 90°. The gait analysis during walking and that during riding may thus be obtained and the movement of walking or riding may be distinguished in accordance with the knee signal because when the feet generate periodic knee signals and sock signals on both feet are "0", it can be affirmed that the user is riding a bicycle. Thus this may also be used for distinguishing user's behavioral state.

The gait during walking or riding a bicycle will definitely be affected by the road conditions. Cameras, accelerometers or gyroscopes may be used in embodiments of the present invention to detect road conditions and improve the accuracy of gait recognition. For example, when the bicycle goes through a pothole or a person suddenly falls, the accelerometers or gyroscopes will gain considerable acceleration (such as a gravitational acceleration or above) or change in angle and images taken by the camera will present dramatic changes. The microcontroller can suspend gait recognition at this moment, in order to avoid misjudgment and meanwhile record the road conditions.

Preferred Embodiment 4

Figure 22:
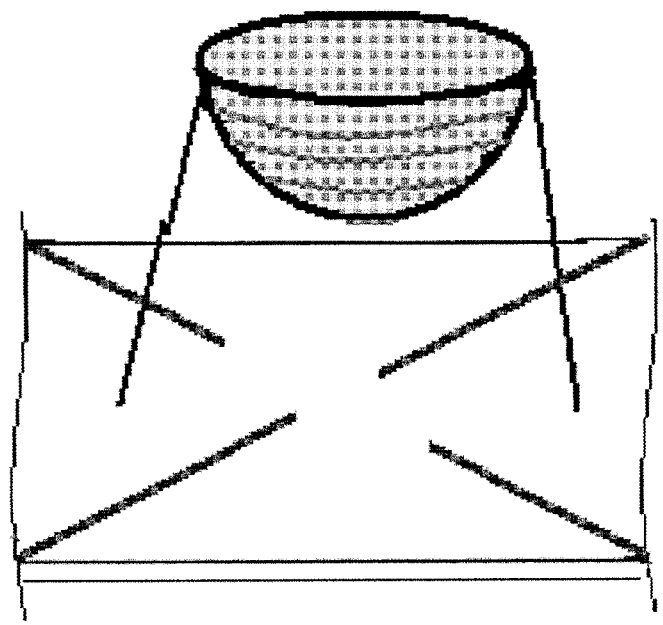
FIG. 22 illustrates a diagram of pressure sensor output in multiple phases in accordance with one embodiment of the present invention.

If necessary, a digital sensor can output in some three stages, as shown in FIG. 22. The center of the digital sensor is a spherical raised conductive material embedded with circular conductive rubber or silicone. Below it there is cross-shaped conductor and there is no conductor in the middle part. When the sphere is lightly pressed, the lowest circular conductive rubber in the sphere contacts the lower conductor but the higher circular conductive rubber in the sphere doesn't contact the lower conductor and thus only one set of conductors are conducted; when the raised part is heavily pressed, both the two raised higher and lower circular conductive rubber components will contact the lower conductor and thus two sets of conductors are conducted; and the raised part is pressed more heavily, three sets of spherical raised conductive materials will be connected. Therefore in gait analysis, the same point, for example the heel, doesn't only present results "0" or "1" but different performance due to different pressure or force. For instance, when the pressure is greater than 20 kg, the first set of spherical raised conductive material is conducted, when the pressure is greater than 40 kg, two sets of spherical raised conductive material are conducted and when the pressure is greater than 60 kg, three sets of spherical raised conductive material are conducted. Thus, the gait analysis results may be better presented and the performance of the center of pressure (COP) could be more meaningful. Every point in FIG. 10A can present pressure changes. The weight is 0 when there is no external force, 1 when there is pressure of 20-40 kg, 2 when there is pressure of 40-60 kg and 3 when there is pressure greater than 60 kg. Thus, there are four kinds of changes that can be presented in the point of heel, rather than "0" or "1." The center of mass (COM) will be more meaningful too. Through the center of mass (COM) or center of pressure (COP), both changes in the user's feet in gait analysis and pressure changes of different points of sole during the gait cycle can be observed. Therefore each point should be weighted (take the weight value of 2 when pressure is 40-60 kg) in analysis of the mass center (COM), total pressure, posture state and total movement mass. In addition, we may also obtain the impulse change through the formula $\int F*^\Delta t = MV$, where F refers to the applied force, M refers to the mass of user, V refers to the velocity, $^\Delta t$ refers to the action time. The result $F*^\Delta t$ refers to the impulse, momentum=mv. For example, when foot is stepped on the ground, the heel will aggravate the force from 0 kg to 60 kg. As described earlier, in such changing time, force carried by the heel is changing over time, resulting in change of three stage pressure sensors. Thus the product of external force and time, namely the impulse can be obtained. It is not just the analysis of center of pressure, the impulse time analysis diagram, F force time analysis diagram, P (momentum) time analysis diagram and F=ma, a acceleration may also be obtained. Thus, we learn that the change of momentum is equal to the value of the impulse.

Preferred Embodiment 5

Figure 23:
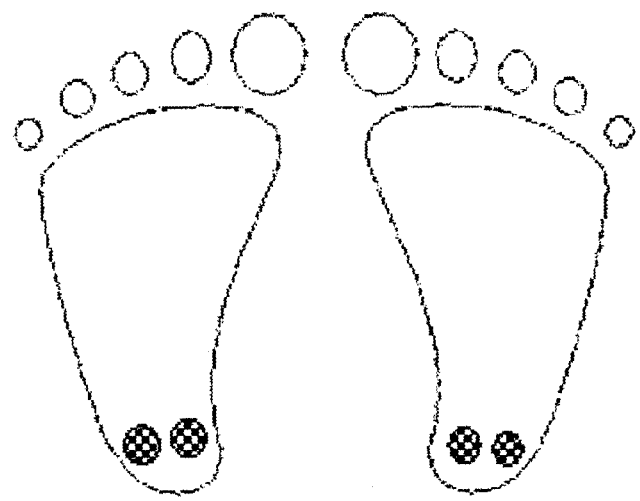
FIG. 23 illustrates a diagram of setting two sensors in the position of heel for observing the time difference between inside and outside contact to earth in accordance with one embodiment of the present invention.

Two or more digital sensors can be mounted to the position of heel for identifying if the inner side or outside contacts the ground first (intoed gait or out-toe gait) during walking, as shown in FIG. 23. For normal people, the time difference in both heels as shown by digital sensors should be within a very small range. Too great time difference may suggest foot injury or disease. Similarly, more sensors may be put in socks so that we may detect a three-dimensional gait analysis diagram for each foot rather than a straight line of signal.

Preferred Embodiment 6

Embodiments of the present invention may also be applied in computer games in connection with physical interaction to input body movements into computer and increase the player's pleasure. For example, show the signals of the arms and the body with jacket. Some gaits that will rarely occur in daily life might occur in games. For example, when we walk to the left or right side, four sensors on both feet almost touch the ground or are lift off simultaneously; for example, for high jump, with knees being bent, the four sensors on both feet are normal; and when we sit down with both knees being bent, the sensors on both feet are abnormal, for example, fall which is common for the elderly or children. Therefore the system can analyze the behavior patterns of users or animals and raise a warning if there is any danger. For such application purposes, clothes, socks, shoes, control boxes, or mobile phone may be installed with camera, accelerometer, magnetometer or gyroscope, to increase the strength feeling of game analog and compensate for the shortcomings of digital sensing. Meanwhile, this can increase the accuracy of real gait analysis or exercise physiology. In addition, the retuning to zero and calibration of accelerometer, magnetometer or gyroscope should have a reference point. The sensing signal for both feet is "0", which means that both feet are on the ground and the center of gravity is the center of the left and right feet.

Preferred Embodiment 7

Before embodiments of the present invention are accomplished, unfavorable conditions are hard to avoid. For example, signal error action of sensor might occur if the clothing, pants or socks are not worn off center or deviated from original position after strenuous exercise. The most common error is bounce, which is similar to that of mechanical switch. In form, it is impulse of extremely short period (less than 0.01 second). To reduce error actions, embodiments of the present invention have summed up the following rules after considering the conditions of normal human body, so as to conduct pre-processing of signal output by various sensors.
1. When the large-angle joint sensors are opened, the small-angle joint sensors must have been opened;
2. With the body's inertia and the strength of ordinary people, extending legs, bending knees, lifting feet, stepping on ground and other movements cannot be completed within K seconds; for young people, K=0.1 second; for the elderly, K=0.15 second, and for Alzheimer's disease patients, K=0.2 second.

According to the above rules, embodiments of the present invention define the pre-processing procedure of signals from all sensors as follows:

1. All positive and negative pulses of less than K seconds in the aforementioned movement cycle are eliminated. K here is set as 0.001 second.
2. For small angle joint sensors, if any signal indicates that it is not opened while the greater angle joint sensors are opened, modify the signal of small angle joint sensors as being opened.

Preferred Embodiment 8

Figure 24:
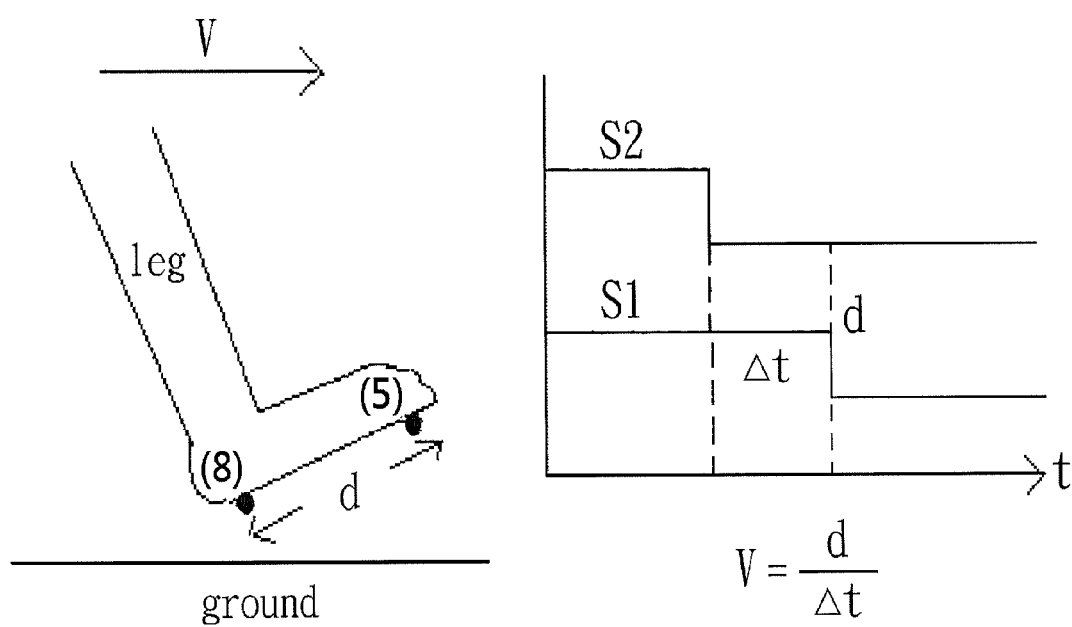
FIG. 24 illustrates a diagram of using the time difference of sensor to estimate the walking speed in accordance with one embodiment of the present invention.
Figure 25:
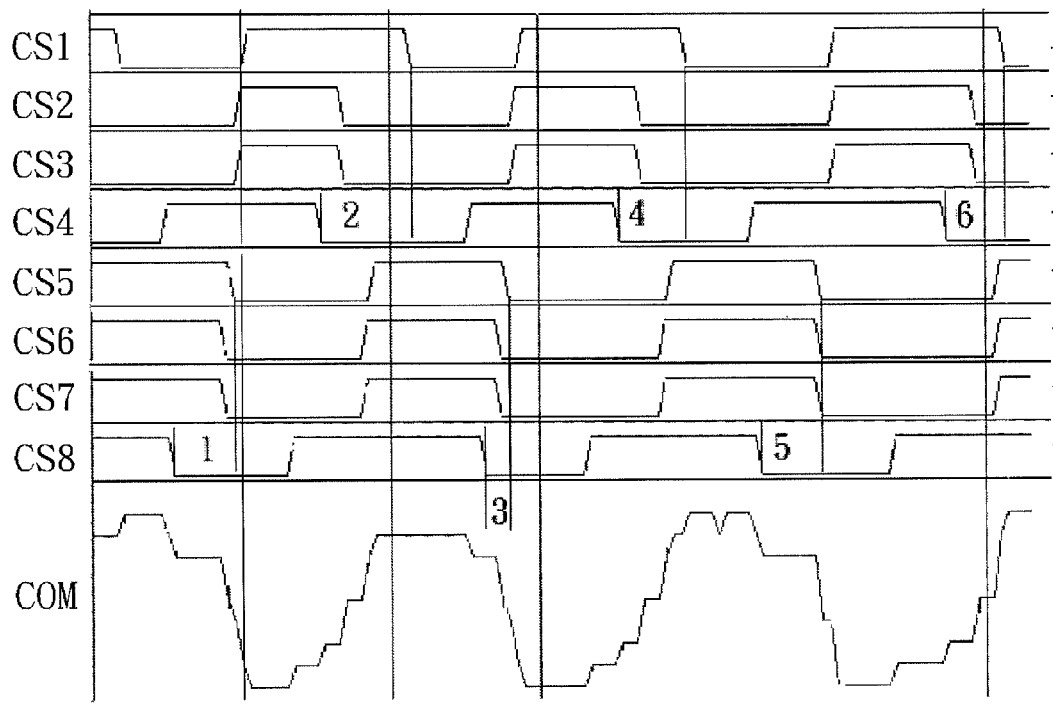
FIG. 25 illustrates a sequence diagram during walking on a treadmill (speed set to 2 km/hr) in accordance with one embodiment of the present invention.

Embodiments of the present invention estimates the walking speed and obtains an approximate value based on the touchdown time difference between heel and tiptoe. As shown in FIG. 24, digital sensors (S2 and S1) are installed in the positions of heel and toe and the distance between both sensors is the foot length d. When the user walks forward at the velocity V, we predict that the speed V' of the feet's touching the ground is similar to the walking speed V. The touchdown time difference between the two sensors S2 and S1 as shown in FIG. 24 is $\Delta t$. The speed V' is thus V'=d/$\Delta t$. In addition, in the formula V"=V'+at, a refers to the acceleration, t refers to the time difference between the left foot and right foot, V' refers to the measured speed of the left foot, and V" refer to the measured touchdown speed of the right foot. Thus, the time t when the user moves from the left foot to the right foot and also the acceleration a can be obtained. Then s (displacement) can be obtained by using the formula: s (displacement)=V't+½a t2. Hence, we may monitor the stride length, velocity and acceleration of both feet, and thereby measure the displacement and distance. Similarly, the displacement, distance, stride length, velocity and variability of acceleration can be detected. The state of user can then be available based on analysis of such information. In case more accurate speed is required, the user may record the time difference of at least two different speeds by using fixed speed treadmill. Obtain a closer result by using the interpolation in practical applications or use the camera accelerometer or gyroscope to assist in correction of the accuracy. Take the sequence diagram (FIG. 25) of a user's walking on a treadmill (with speed being set as 2 km/hr) as an example: the time differences between sensors S1 and S2 in steps 1 to 6 are 0.32, 0.50, 0.15, 0.35, 0.31, 0.30 second in order, the difference between sensors S1 and S2 is 20 cm, the converted walk rates are 2.0, 1.28, 4.26, 1.83, 2.06, 2.13 km/hr. In addition, the time required by each step among the six steps is respectively: 0.8, 0.88, 0.57, 0.57, and 1.15 seconds. Thus, the acceleration of each step is: −0.9, 3.39, −4.26, 0.4, 0.06 Km/hr·sec. The corresponding step length is: 0.52, 0.67, 0.48, 0.34, and 0.69 meters. The measured acceleration from step 1 to step 2 is −0.9, the acceleration from step 2 to step 3 is 3.39. The increased step of step 2 is 0.67, more than step 1 as a result of greater imbalance of human body for achieving synchronism with the treadmill. The acceleration of step 6 is 0.06, which indicates that the user has adapted to the speed of the treadmill and achieved synchronism with the treadmill. In gait analysis, we can use these parameters to judge if a person's gait is stable. Too significant change might be the premonition of falls and warning would be raised accordingly. We can use it as an input means of virtual games, and use the previous, current and future signal from the sensors of the right foot to calculate the velocity, acceleration, displacement and distance. The velocity, acceleration and displacement can be measured in different touchdown sequences by using sensors of both feet. Similarly, part of the sensors can be installed in socks and other part in shoes or insoles.

The angular velocity of joint can also be assessed. For instance, the threshold angle of a sensor at knee joint is set at 45°, the angle of knee when the foot of the same leg is just leaving, and 60°, the largest bending angle of the knee, then the angular velocity can be obtained by W=θ/t, where t refers to the time difference between the turn-on time of 45° and 60° sensors, L refers to the length of shank, θ is 15°, and L*θ refers to the distance for swimming from 45° to 60°. L*W can be used for calculating the swing angular velocity of feet. Thus we can measure the parameters such as swing distance, swing angle, swing angular velocity or swing angular acceleration of posture changes in the swing phase and assess the user's stability and variability. Similarly, by the sensor at the hip joint we can also detect the angular velocity of the foot, and the whole hip joint angular acceleration by L*W, where L is the length of the whole foot.

Figure 26A:
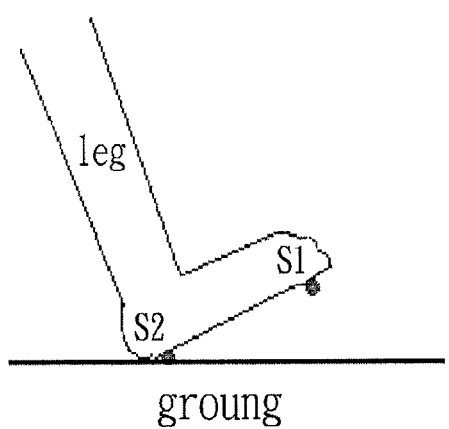
FIG. 26A, FIG. 26B illustrate slope detection diagrams in accordance with one embodiment of the present invention.
Figure 26B:
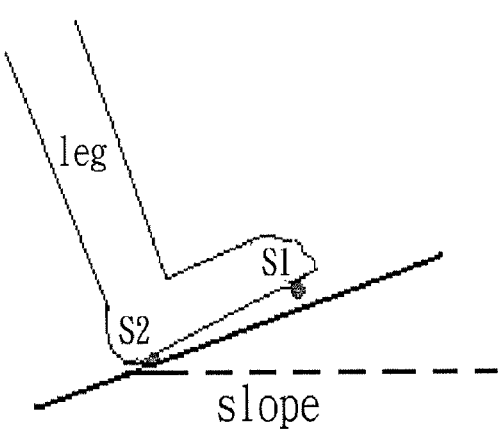

For the ankles we can place two sensors to detect the angles. For example, two sensors (S1 and S2) in the positions of heel and the side respectively represent the time difference Δt of start between two sensors when the heel is down (10°) and the foot is on the ground (0 degree). Hence, the angular velocity of the ankle joint can be calculated by using the formula W=10/Δt. As shown in FIGS. 26A and 26B. Of course, part of the sensors can be installed in socks and other part in shoes or insoles. For other locations such as ribs, knees and so on, the same result will be obtained. In addition, we can also use a sensor of two stages or more other than two separate sensors (S1 and S2) to obtain the same effect, namely, detect the angle, angular velocity, angular acceleration, swing distance, swing angle, swing angular velocity or swing angular acceleration. Similarly, the variability of the angle, angular velocity, angular acceleration, swing distance, swing angle, swing angular velocity or swing angular acceleration can also be detected. Therefore, we can set a tension or pressure sensor in socks or part of the socks and the other part in shoes or insoles, so as to detect the angle, angular velocity and angular acceleration. For other locations such as rib, elbow, knees, hip joint and so on, the same result will be obtained.

Going uphill will be affected by slope as it is no longer the same as walking on flat ground. Thus, the movement of going uphill may be judged based on the time difference. As shown in FIG. 26A and FIG. 26B, assuming that the foot conducts constant circular motion during the period from the heel's touching the ground to the tiptoe's touching the ground and the sole of foot and the ground is angle θ (10°) when the heel touches the ground in normal walking state, the ground touching time difference of the sensors S1 and S2 is Δt, and the uphill time difference is Δt', then the ground slope can be obtained as θ*(Δt−Δt')/Δt.

In short, the foot velocity V may be obtained based on the landing time difference between S1 and S2 on two points in the sole of foot. The landing time difference Δt1 of both feet, velocity V2 of the right foot and velocity V1 of the left foot can be measured. The accelerational for landing of both feet can thus be measured by using the formula V2=V1+a1*Δt1. Otherwise, the velocity a2 for two times' landing of the left foot can be measured by using the formula V3=V1+a2*Δt2 (The landing time difference Δt2 of the left feet in two continuous times' landing, velocity V3 of the left foot next time can be measured). In principle, Δt2 is approximately equal to 2*Δt1. Thus, embodiments of the present invention may measure the acceleration during movement and speed of each time and carry out statistics to obtain the variability. The variability may be used to determine if the gait of user is stable and predict the gait of the next step because the velocity will remain stable if the acceleration and variability velocity are fixed and changeless, the velocity also remained stable. Furthermore, when the velocity, acceleration, and time difference are stable, the walking distance of the next step may be predicted using the formula S=V*t+0.5*a*t2. The displacement may be obtained by using the formula ∫v*$^\Delta$t=s. Meanwhile in this process, the walking distance can be obtained. On the other hand, if the acceleration, velocity, distance and other values vary greatly, it might suggest that the gait of the user is abnormal and warning has to be raised. For example, the user might have suffered from falls or run into other people or things.

∫F*$^\Delta$t=MV may be used to calculate the impulse change, where F refers to the force, M refers to the mass of the user, V refers to the velocity, $^\Delta$t refers to the acting time and F*$^\Delta$t refers to the impulse. The time analysis diagrams of impulse, force F, p(momentum)=mv and f=ma may also be obtained. Thus we can once again verify a and V0, where V=V0+at.

Similarly, at least two stages of angle sensors in the position of a joint may be used to measure the angular velocity of the joint. The angular acceleration (α) can be calculated based on the value of the current and next time angular velocities and time differences. In such circumstances, if the variability of angular acceleration or angular velocity is very small, the angular velocity of the next joint movement may be predicted based on the current time angular velocity. The swing length may be calculated by using the formula L=R*θ, where R is the length of the leg or arm where the joint is located; and θ refers to the changing angle. The swing length L can be predicted if the angular velocity and angular acceleration remained stable (low variability).

So we can get, V=V0+at;

$S=S0+V0t+\tfrac{1}{2}at2;$ $V2=V02+2a(S-S0);$ $\omega=\omega0+\alpha t;$ $\theta=\theta0+\omega0t+\tfrac{1}{2}\alpha t2;$ $\omega2=\omega02+2\alpha(\theta-\theta0);$ ∫w*$^\Delta$t=θ, thus we can get the angle and time analysis diagram.

According to the law of conservation of energy, mechanical energy E of a system is equal to the sum of potential energy U and kinetic energy K of objects in this system, namely, E=K+U, U=mgh (h is height), K=½ m v2. That is to say, the change of the total energy (ΔEmec) contains ΔK (the change in kinetic energy) and ΔU (the change in potential energy) and is a constant. Thus, we can obtain the change h in height of user in daily life.

In the law of conservation of energy, p refers to the momentum.

$$\sum_{i=1}^{N} p_i = \text{constant}$$

or $$\frac{d}{dt}\sum_{i=1}^{N} p_i = 0$$

In a rotating system, relationship between force (F) and torque (τ); and that between momentum (p) and angular momentum (L) are as follows, the angular momentum (L) remains changeless when the combined external torque (τ) carried by the system is zero.

$$\frac{dL}{dt} = r \times F$$

And the angular momentum (L) doesn't change over time when the right torque (τ) is zero. The angular momentum L=r*mv=constant when the combined external torque (τ) carried by a human body is zero.

The total kinetic energy of rolling human body is the sum of the translational energy of the center of mass and kinetic energy of rotation around the center of mass.

$$K = \tfrac{1}{2}I\omega2 + \tfrac{1}{2}\,m\,v2$$

The body move with both rotation and translation at the same time, for example, when the right foot just leaves off the ground, left foot acted as a fulcrum and the center of gravity in this fulcrum of rotation, and the right foot translateed forward. The work can be written as W=K (translation kinetic energy)+KR (rotation kinetic energy)

TABLE 2

A comparison of movement and rotation kinetic equations a

|  | Rotation along a fixed axis | Translational movement |
| --- | --- | --- |
| Kinetic energy | $KR = \tfrac{1}{2} I\omega2$ | $K = \tfrac{1}{2}\,mv2$ |
| Balance | $\Sigma\tau = 0$ | $\Sigma F = 0$ |
| Newton's second law | $\Sigma\tau = I\alpha$ | $\Sigma F = ma$ |
| Newton's second law | $\Sigma\tau = dL/dt$ | $\Sigma F = dp/dt$ |
| Momentum | $L = I\omega$ | $p = mv$ |
| Conservative Theorem | $Li = Lf$ | $pi = pf$ |
| Power | $P = \tau\omega$ | $P = Fv$ |

Both movement and rotation kinetic equations are expressed in vector based form. Only part of rotation equations are expressed in non-vector based form.

$$K_R = \sum_i K_i = \sum_i \tfrac{1}{2} m_i r_i^2 \omega^2$$

$$K_R = \tfrac{1}{2}\left(\sum_i m_i r_i^2\right)\omega^2 = \tfrac{1}{2} I\omega^2$$

The total rotation kinetic energy of rigid body is the sum of rotation kinetic energy for all particles in the rigid body. Where I refers to the momentum of inertia (moment of inertia)

Law of conservation of moment of inertia $I1\omega1 = I2\omega2$

When the user rotates and translated at the same time, the above parameters such as ω, α, v, and a can be measured. If necessary, we can increase the accuracy of the signal by introducing accelerometer, gyroscope, or tilt sensor. The Work can be written as W=K (translatiobnal kinetic energy)+K R (rotating kinetic energy). Furthermore, considering the height of center of mass is changing during walking, we can give E=W+U, where U=mgh, where h is the height of the center of gravity.

Embodiments of the present invention can be used to estimate the slope of going uphill or downhill or slope of going upstairs or downstairs and get an approximation based on the length of time when sensor at the knee joint is opened. Where the slope is greater, legs have to be lift up higher, the knee joints have to be bent greater, and the sensor at the knee joint has to be opened for a longer time. Of course, we can also set multiple stage sensors in pants, such as 45°, 60° and 75° three stages; when the knee joint starts to be bent from the straight state, 45° sensor generates "1" at first and then both 45° sensor and 60° sensor generate "1". If even 75 degree sensor generates "1", it represents a greater flexion angle, namely, a greater slope.

Preferred Embodiment 10

Figure 27:
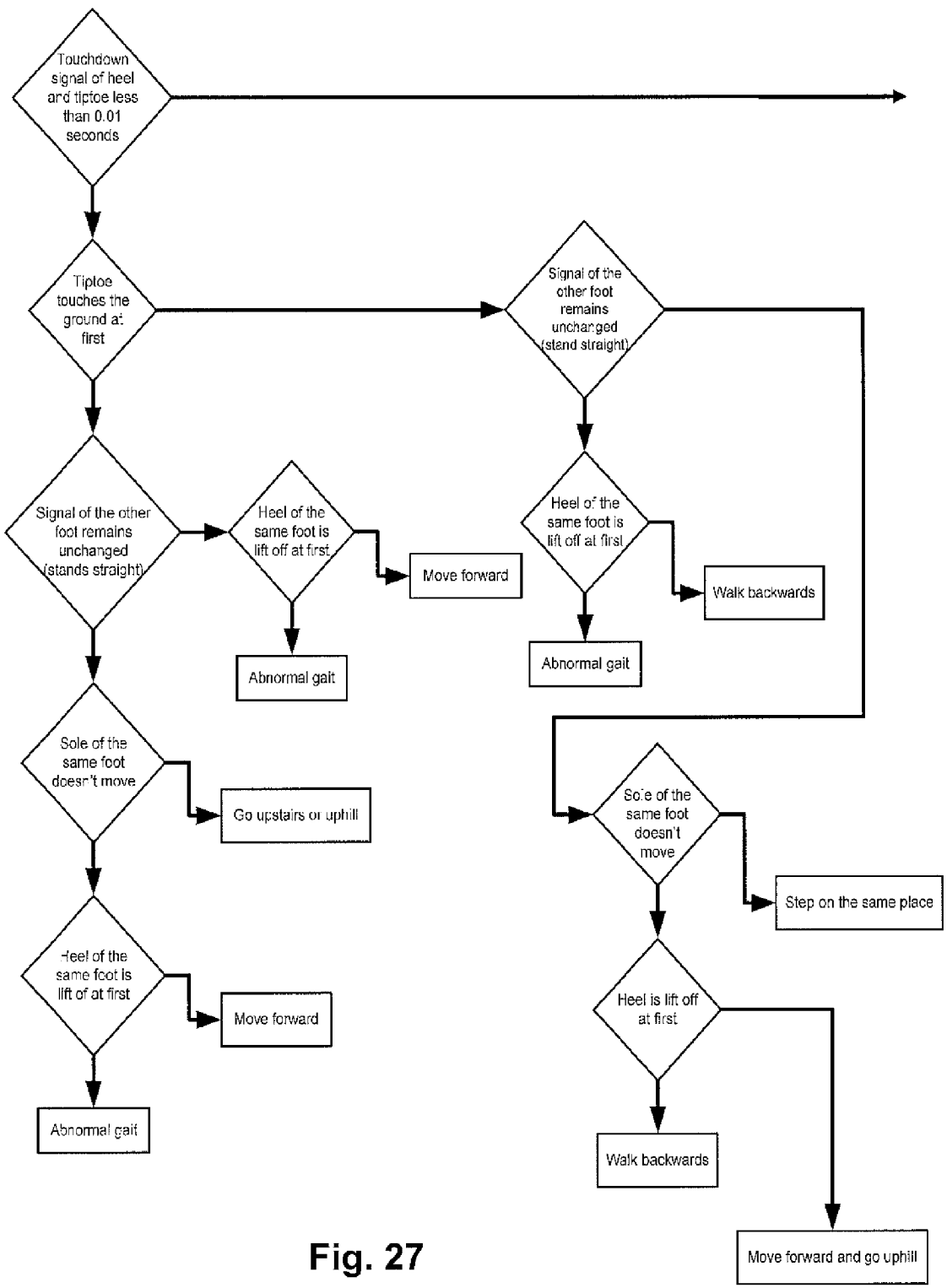
FIG. 27 illustrates a flow chart of gait analysis in accordance with one embodiment of the present invention.
Figure 27:
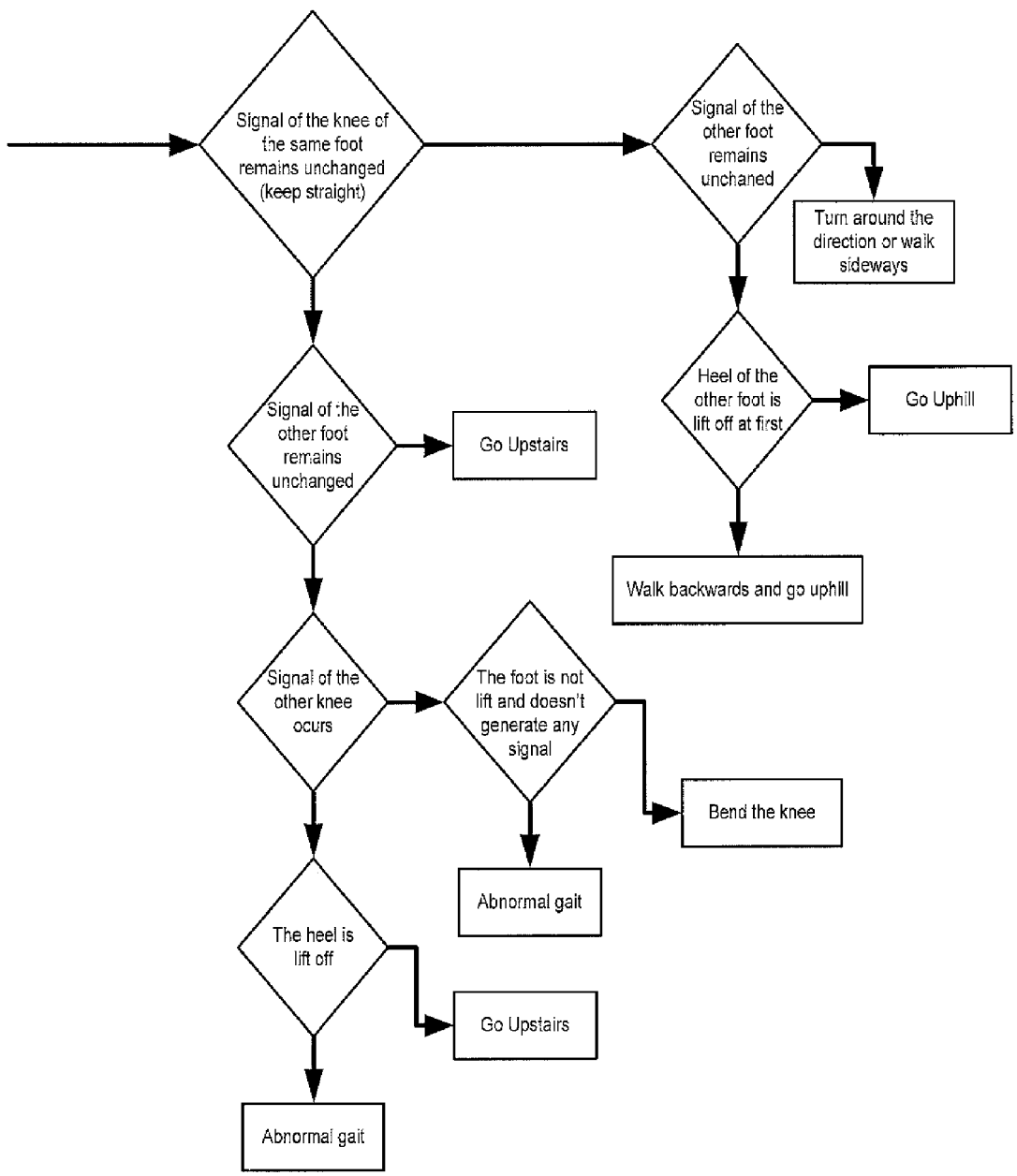
Figure 28:
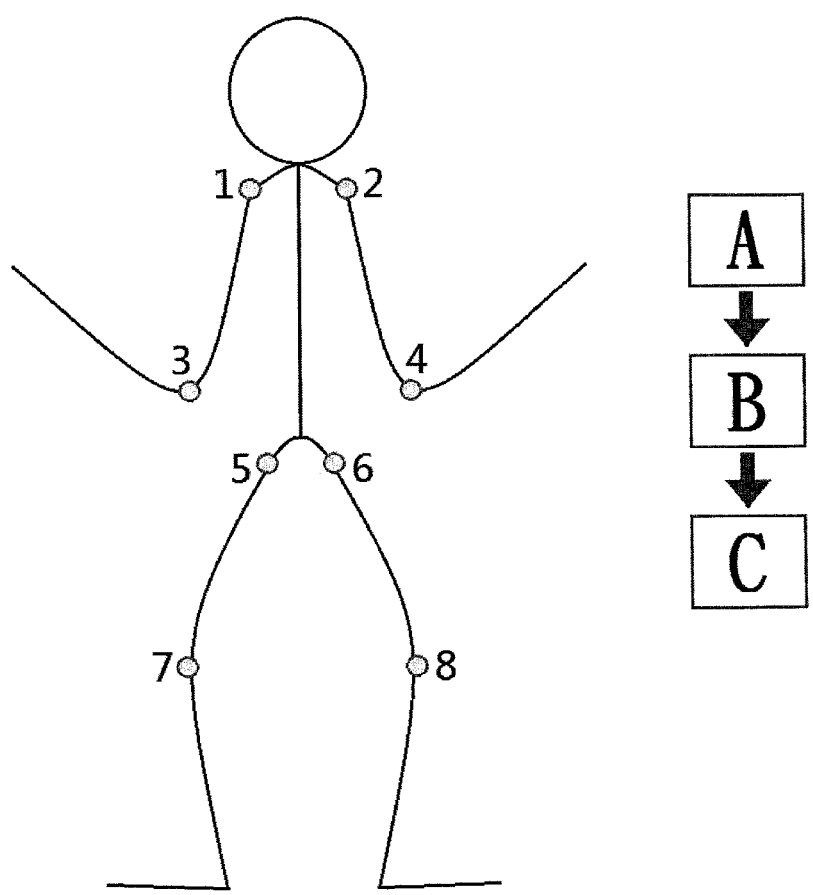
FIG. 28 illustrates a diagram of posture identification in accordance with one embodiment of the present invention.
Figure 29:
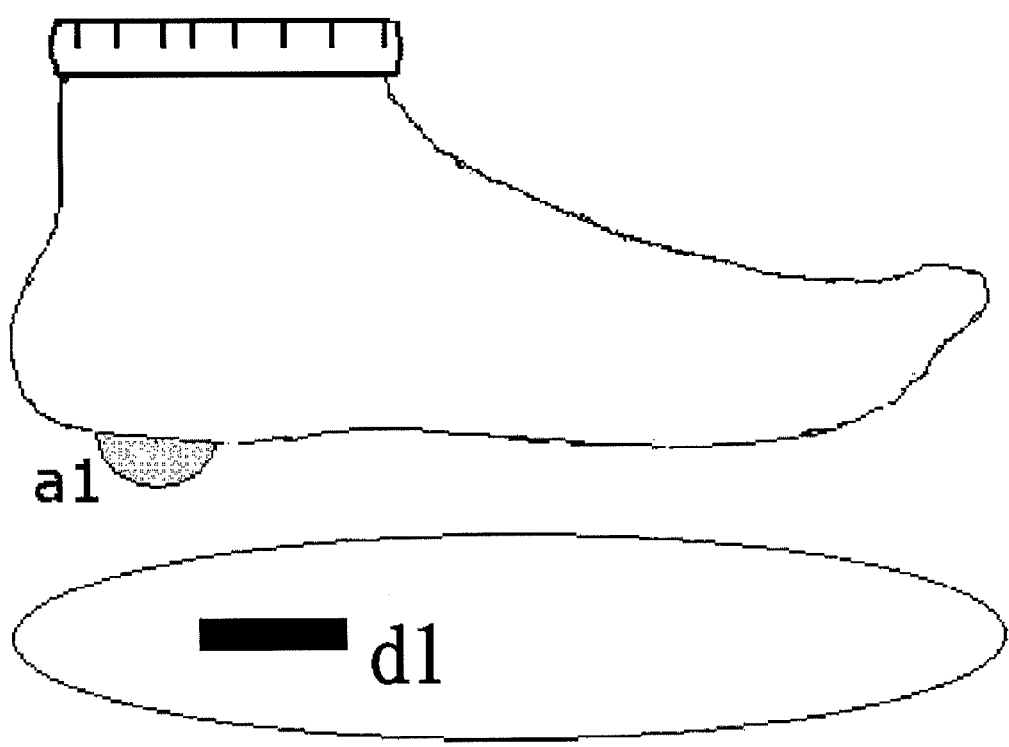
FIG. 29 illustrates a diagram of another embodiment of socks and insoles in accordance with one embodiment of the present invention.

The process of gait analysis is as shown in FIG. 27. When a user walks forward, his/her heels touch the ground at first while when he is going uphill, the touchdown time difference between the heel and the tiptoe is shorter. Conversely, the tiptoe touches the ground first if a user is walking downhill, and in case of greater downhill angle, the pressure distribution of tiptoe and heel would be opposite, namely, the pressure is transferred to the tiptoe, just like wearing high heels. If coupled with the changes in upper body postures, as shown in FIG. 28, where, A means that sensor may show corresponding reaction when the posture of user is changed and on/off and other associated signals are received based on information provided by various sensors (installed to the body); B means that a database is provided to compare on/off and other associated signals so as to determine the changes in user's posture; and C refers to 3D three-dimensional information about the simultaneous posture changes of a user being provided to ensure that the detected posture changes of user are more accurate and the posture state of the person may be learnt, as shown in Table 3.

TABLE 3

| Database | Posture |
| --- | --- |
| 11110000 | Sitting, hands naturally hang |
| 11111010 | Sitting, with elbows being bent |
| 00000000 | Standing, hands naturally hang |
| 00001010 | Standing, with elbows being bent |

Among them, in the database the 8-bit strings from right to left respectively stand for right axilla, right elbow, left axilla, left elbow, right hip, right knee, left hip, and left knee. For example, when high heels touch the ground, the thumbs of feet touch the ground first and the weight of body is kept in front of feet.

When a user wears different styles of shoes, the present shoes may learn the style of shoes with the aid of gait analysis signal, such as high heels, low cutters, slippers, sneakers and skating shoes etc. For example, when high heels touch the ground, the thumbs of feet touch the ground first and the weight of body is kept in front of feet. Most signals are obtained from digital switches and tension and pressure sensors. For example, use a conductive fabric to form a capacitor together with the body or upper and lower two conductive materials (such as two pieces of conductive fabrics) to form a capacitor and generate capacitance change by means of external force. Meanwhile, part of the sensors can be separately installed in socks or one sock and the other part in shoes or insoles to form analog switches and tension or pressure sensors. The inductive sensors are as shown in PCT/CN2008/001520 or PCT/CN2008/001571. If a magnetic material is located in a sock, shoe, or insole, and a conductive material such as coil is winded outside the sock, upper of shoe or insole, the induced electrodynamics force is not the same if the magnetic flux is different by external force. Thus, we can also obtain the value of energy generated by related movement.

Sensors in all the above-mentioned embodiments can be installed with part in socks and the other part in shoes or insoles, so do the analog switches, tension or pressure sensors, such as capacitive or inductive switches or tension or pressure sensors. In addition, when all sensors are installed in socks, they should also be capacitive or inductive switches, or tension or pressure sensors.

Preferred Embodiment 11

There is a raised conductive material a1 in sock. Accordingly, there is a perforation d1 in a shoe or insole with conductive material on the perforation edge or periphery. Material interaction: when a1 is magnetic material and the perforation d1 is surrounded by a coil, an induced current could be produced and stored when the user is walking. Among the above-mentioned sensing components in socks and shoes or insoles, when the process is connected to switch sensor or pressure or tension sensor with transmission line, a reference area is to be set in the surrounding area where the transmission line is not insulated for detecting leakage of fabrics, for example, the fabric is too wet or the transmission line and the reference area suffer from short circuit. Reference area can be set beside any guide wire of the circuit installed in fabrics for detecting electrical leakage. The reference area itself can also be used as electrodes, heater wire or antenna. Positions of the sensing components in socks and shoes or insoles as shown in above FIG. 29, FIG. 16, FIG. 17 and FIG. 18 are interchangeable.

Preferred Embodiment 12

Figure 30:
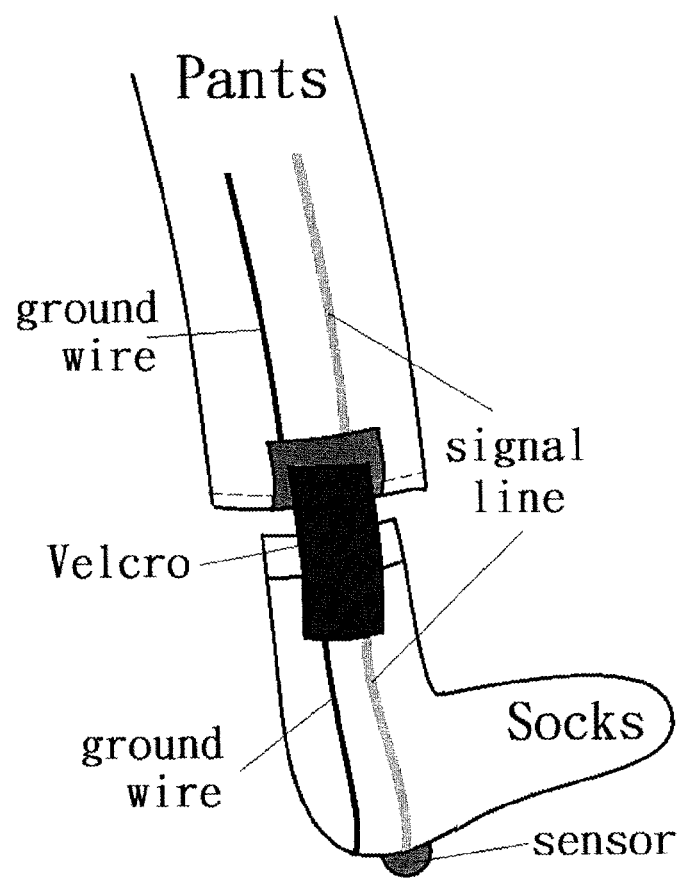
FIG. 30 illustrates a diagram of connecting pants and socks with Velcro in accordance with one embodiment of the present invention.

Stainless steel wire and other conductive material can be used as transmission line and socks, clothing, or pants can be used as circuit board. Connect stainless steel wire and microcontroller or, socks, clothing and pants with common press buttons or snap buttons. Here we use Velcro to connect transmission lines between socks and pants, or pants and clothing or inner and outer clothing. Finally, Velcro is used to fabrics textiles such as socks, pants, clothing, bed sheets, chairs and shoes to the control box (containing the processor). For example, as shown in FIG. 30, the output lines (one ground wire and one signal wire) of sensors in socks are connected to Velcro. The corresponding ground wire and one signal wire in pants may transmit sensor signal to pants through Velcro. In other words, set one Velcro with at least one transmission line, such as stainless steel wire or other conductive material in socks, and also set one Velcro with at least one transmission line, such as stainless steel wire or copper wire in pants. Transmission lines between socks and pants can be connected after the Velcros of socks and pants are connected and thereby the signal or current between them can be connected with each other and the Velcro can be used as connector. In addition, Velcro is also connected to socks or other clothing with a strap, so as to increase the ° of freedom between the socks and pants. The above-mentioned sensors can be sensors that output physiological signals such as heartbeat or breathing or sensors that output posture signals such as tension or pressure sensors or switches. Velcro can be used to transmit the above mentioned signals or current, such as heating or cooling clothing TENS. Similarly, it can be set between pants and clothing or bed sheet and clothing.

Preferred examples of embodiments of the invention are given to describe the characteristics and spirit of this invention more clearly, and are not intended to limit the scope of the invention in any form. On the contrary, their objectives are to include all changes and corresponding arrangements the prospective scope of the invention.

What is claimed is:

1. A system for analyzing gait using textile sensors, comprising:
   a sock sensing system, which comprises a sock and at least one switch, tension sensor, or pressure sensor for sensing a posture or movement; and
   a processor configured to receive signals from the sock sensing system and to analyze a gait parameter, wherein the processor is configured to calculate the gait parameter using a signal from the sock sensing system as a trigger point.

2. The system for analyzing gait of claim 1, wherein the sock sensing system further comprising a shoe or an insole.

3. The system for analyzing gait of claim 2, wherein at least one sensor is installed in the sock, the shoe or the insole,
   wherein the at least one sensor comprises at least one conductive material installed in the sock, and at least one corresponding electronics installed at at least one corresponding position in the shoe or the insole; or
   wherein the at least one sensor comprises at least one electronics installed in the sock, and at least one corresponding conductive material installed at at least one corresponding position in the shoe or the insole.

4. The system for analyzing gait of claim 2, wherein the sensors are installed in socks, shoes or insoles, one conductive material is installed in a sock and a variable resistor, piezoelectric material, variable capacitor or variable inductor is installed in the lining of the corresponding shoe or insole.

5. The system for analyzing gait of claim 1, wherein the variation of the frequency, period, voltage, or current of the signal sensed by the sock sensing system are used to analyzed the gait of the user.

6. The system for analyzing gait of claim 5, wherein charge/discharge, alternating current, or direct current model are used to analyze the frequency, period, voltage, or current of the signal sensed by the sock sensing system.

7. The system for analyzing gait of claim 6, wherein an electronic switch is used to speed up the discharge process.

8. The system for analyzing gait of claim 1, wherein the stride length, velocity, acceleration, displacement, or walking distance may be obtained; the angle, angular velocity, angular acceleration, swing distance, swing angle, swing angular velocity, swing angular acceleration of a joint may be obtained.

9. The system for analyzing gait of claim 1, wherein the ground slope may be detected.

10. The system for analyzing gait of claim 1, wherein the textile sensors are digital switch, digital tension sensor, digital pressure sensor, analog switch, analog tension sensor or analog pressure sensor.

11. The system for analyzing gait of claim 1, wherein there are at least two textile sensors that may sense the posture or movement of human body and at least one textile sensor is connected with an electronic component in series or parallel so that two wires being connected to processor may read the logic state of each textile sensor.

12. The system for analyzing gait of claim 11, wherein the electronic component is a resistor, inductor, capacitor, diode, transistor, amplifier, or integrated circuit.

13. The system for analyzing gait of claim 1, wherein the center of pressure, center of mass, total pressure, posture state, total movement mass, impulse, force, torque, momentum, angular momentum, weight, rotor inertia, potential, kinetic energy can be obtained by using sensor.

14. The system for analyzing gait of claim 1, wherein the type of shoes worn by the user can be sensed.

15. A method for analyzing gait using textile sensors, comprising:

detecting, using a processor, a signal of a posture or movement change generated by a sock sensing system comprising the processor and a sensor in a sock, in a sock and shoe combination, or in a sock and insole combination, analyzing the signal to generate a gait parameter, wherein the gait parameter is generated by a program processing module and the gait parameter is calculated using a signal from at least one sensor in the sock sensing system as a trigger point.

16. The method for analyzing gait using textile sensors of claim 15, wherein changes in bending angle of knee or hip joint can be predicted based on the generated gait analysis parameters; or the posture or state of feet can be sensed by using the knee or hip joint sensor.

17. The method for analyzing gait using textile sensors of claim 15, wherein an accelerometer, tilt sensor, video camera or gyroscope is connected to the processor in order to improve the accuracy of sensing body movement.

18. The method for analyzing gait using textile sensors of claim 17, wherein the processor may use the sensors below feet as reference points to correct signal from the accelerometer, tilt sensor, video camera or gyroscope for reading the angle, signal or displacement.

* * * * *